(12) United States Patent
Caspers

(10) Patent No.: US 7,922,775 B2
(45) Date of Patent: Apr. 12, 2011

(54) PULSATING PRESSURE CHAMBER AND METHOD FOR FLUID MANAGEMENT

(75) Inventor: Carl A. Caspers, Avon, MN (US)

(73) Assignee: Otto Bock Healthcare LP, Minneapolis, MN (US)

( * ) Notice: Subject to any disclaimer, the term of this patent is extended or adjusted under 35 U.S.C. 154(b) by 553 days.

(21) Appl. No.: 10/445,176

(22) Filed: May 23, 2003

(65) Prior Publication Data
US 2004/0030411 A1 Feb. 12, 2004

Related U.S. Application Data

(63) Continuation-in-part of application No. 10/090,971, filed on Mar. 4, 2002, now Pat. No. 6,926,742, which is a continuation-in-part of application No. 09/785,714, filed on Feb. 16, 2001, now Pat. No. 6,726,726, which is a continuation-in-part of application No. 09/492,406, filed on Jan. 27, 2000, now Pat. No. 6,508,842, which is a continuation-in-part of application No. 09/325,297, filed on Jun. 3, 1999, now abandoned.

(60) Provisional application No. 60/383,159, filed on May 23, 2002.

(51) Int. Cl.
*A61F 2/80* (2006.01)
*A61H 7/00* (2006.01)
(52) U.S. Cl. .................. 623/34; 623/36; 601/9
(58) Field of Classification Search ............ 601/9, 11; 623/FOR. 34, FOR. 36, FOR. 37, 34, 36, 623/37
See application file for complete search history.

(56) References Cited

U.S. PATENT DOCUMENTS

| 980,457 | A | 1/1911 | Toles |
| 2,180,960 | A | 7/1938 | Kennedy |
| 2,424,278 | A | 7/1947 | Kunkel |
| 2,464,443 | A | 3/1949 | Ganoe et al. |
| 2,530,285 | A | 11/1950 | Catranis |

(Continued)

FOREIGN PATENT DOCUMENTS
AU 670631 7/1996
(Continued)

OTHER PUBLICATIONS

English translation of JP 7-155343 A1 (11 pages, including the cover page).*

(Continued)

*Primary Examiner* — David H. Willse
(74) *Attorney, Agent, or Firm* — Holland & Hart

(57) ABSTRACT

An apparatus and method is provided for securing a prosthesis to the residuum of a limb of an amputee and for providing pressure therapy to the residuum so as to manage fluid within the residuum. The apparatus includes a socket shaped to receive a residuum of a limb of an amputee and configured to connect to a prosthetic limb. The socket forms a chamber between the socket and the residuum when the socket receives the residuum. The apparatus also includes a pressure control device operably connected to the chamber and capable of creating a positive pressure and a negative pressure within the chamber to provide pressure therapy to the residuum, as well as provide securement of the socket to the residuum. The apparatus may also include a liner surrounding at least a portion of the residuum. The control device adjusts pressure within the chamber based on manual and automatic inputs.

68 Claims, 17 Drawing Sheets

U.S. PATENT DOCUMENTS

| | | | |
|---|---|---|---|
| 2,531,074 A | 11/1950 | Miller | |
| 2,533,404 A * | 12/1950 | Sharp et al. | 623/36 |
| 2,606,325 A | 8/1952 | Nielson et al. | |
| 2,664,572 A | 1/1954 | Blevens | |
| 2,671,225 A | 3/1954 | Schoene et al. | |
| 2,696,010 A | 12/1954 | Robinson | |
| 2,696,011 A | 12/1954 | Galdik | |
| 2,790,180 A | 4/1957 | Hauser | |
| 2,808,593 A | 10/1957 | Andersen | |
| 3,253,600 A | 5/1966 | Scholl | |
| 3,309,714 A | 3/1967 | Porten | |
| 3,322,873 A | 5/1967 | Hitchcock | |
| 3,377,416 A | 4/1968 | Kandel | |
| 3,393,407 A | 7/1968 | Kandel | |
| 3,403,673 A | 10/1968 | MacLeod | |
| 3,557,387 A | 1/1971 | Ohlenbusch | |
| 3,631,542 A | 1/1972 | Potter | |
| 3,712,298 A | 1/1973 | Snowdon et al. | |
| 3,732,578 A | 5/1973 | Pollack | |
| 3,751,733 A | 8/1973 | Fletcher et al. | |
| 3,858,379 A | 1/1975 | Graves et al. | |
| 3,895,405 A | 7/1975 | Edwards | |
| 3,975,350 A | 8/1976 | Hudgin et al. | |
| 3,991,424 A | 11/1976 | Prahl | |
| 4,029,087 A | 6/1977 | Dye et al. | |
| 4,077,402 A | 3/1978 | Benjamin, Jr. et al. | |
| 4,215,679 A | 8/1980 | Rustin | |
| 4,283,800 A | 8/1981 | Wilson | |
| 4,314,398 A | 2/1982 | Pettersson | |
| 4,381,768 A | 5/1983 | Erichsen et al. | |
| 4,387,472 A | 6/1983 | Wilson | |
| 4,404,296 A | 9/1983 | Schapel | |
| 4,456,642 A | 6/1984 | Burgdorfer et al. | |
| 4,466,936 A | 8/1984 | Schapel | |
| 4,479,272 A | 10/1984 | Beldzisky | |
| 4,623,354 A | 11/1986 | Childress et al. | |
| 4,634,446 A | 1/1987 | Kristinsson | |
| 4,635,626 A | 1/1987 | Lerman | |
| 4,704,129 A | 11/1987 | Massey | |
| 4,738,249 A | 4/1988 | Linman et al. | |
| 4,743,264 A * | 5/1988 | Sherva-Parker | 623/33 |
| 4,822,371 A | 4/1989 | Jolly et al. | |
| 4,828,325 A | 5/1989 | Brooks | |
| 4,888,829 A | 12/1989 | Kleinerman | |
| 4,908,037 A | 3/1990 | Ross | |
| 4,922,893 A | 5/1990 | Wright et al. | |
| 4,923,475 A | 5/1990 | Gosthnian et al. | |
| 5,007,937 A * | 4/1991 | Fishman et al. | 623/34 |
| 5,025,781 A | 6/1991 | Ferrari | |
| 5,108,455 A | 4/1992 | Telikicherla | |
| 5,133,776 A | 7/1992 | Crowder | |
| 5,139,523 A | 8/1992 | Paton et al. | |
| 5,163,965 A | 11/1992 | Rasmusson et al. | |
| 5,186,163 A | 2/1993 | Dye | |
| 5,211,667 A | 5/1993 | Danforth | |
| 5,218,954 A | 6/1993 | van Bemmelen | |
| 5,221,222 A | 6/1993 | Townes | |
| 5,253,656 A | 10/1993 | Rincoe et al. | |
| 5,258,037 A | 11/1993 | Caspers | |
| 5,314,497 A | 5/1994 | Fay et al. | |
| 5,362,834 A | 11/1994 | Schapel et al. | |
| 5,376,129 A | 12/1994 | Faulkner et al. | |
| 5,376,131 A | 12/1994 | Lenze et al. | |
| 5,376,132 A | 12/1994 | Caspers | |
| 5,383,894 A | 1/1995 | Dye | |
| 5,397,628 A | 3/1995 | Crawley et al. | |
| 5,413,611 A | 5/1995 | Haslam, II et al. | |
| 5,443,525 A | 8/1995 | Laghi | |
| 5,464,443 A | 11/1995 | Wilson et al. | |
| 5,480,455 A | 1/1996 | Norvell | |
| 5,507,834 A | 4/1996 | Laghi | |
| 5,514,186 A * | 5/1996 | Phillips | 623/52 |
| 5,534,034 A | 7/1996 | Caspers | |
| 5,549,709 A | 8/1996 | Caspers | |
| 5,571,208 A | 11/1996 | Caspers | |
| 5,593,454 A | 1/1997 | Helmy | |
| 5,658,353 A | 8/1997 | Layton | |
| 5,658,354 A | 8/1997 | Norvell | |
| 5,662,715 A | 9/1997 | Slemker | |
| 5,674,262 A | 10/1997 | Tumey | |
| 5,702,489 A * | 12/1997 | Slemker | 623/34 |
| 5,728,167 A | 3/1998 | Lohmann | |
| 5,728,168 A | 3/1998 | Laghi et al. | |
| 5,728,169 A | 3/1998 | Norvell | |
| 5,728,170 A | 3/1998 | Becker et al. | |
| 5,735,906 A | 4/1998 | Caspers | |
| 5,830,237 A | 11/1998 | Kania | |
| 5,888,216 A | 3/1999 | Haberman | |
| 5,888,230 A | 3/1999 | Helmy | |
| 5,888,231 A | 3/1999 | Sandvig et al. | |
| 5,904,721 A | 5/1999 | Henry et al. | |
| 5,904,722 A | 5/1999 | Caspers | |
| 5,935,146 A | 8/1999 | McEwen et al. | |
| 5,968,073 A | 10/1999 | Jacobs | |
| 5,980,577 A | 11/1999 | Radis et al. | |
| 6,007,559 A | 12/1999 | Arkans | |
| 6,063,125 A | 5/2000 | Arbogast et al. | |
| D429,335 S | 8/2000 | Caspers et al. | |
| 6,106,559 A | 8/2000 | Meyer | |
| 6,117,177 A | 9/2000 | Chen et al. | |
| 6,231,532 B1 | 5/2001 | Watson et al. | |
| 6,231,616 B1 | 5/2001 | Helmy | |
| 6,231,617 B1 | 5/2001 | Fay | |
| 6,273,918 B1 | 8/2001 | Yuhasz et al. | |
| 6,287,345 B1 | 9/2001 | Slemker et al. | |
| 6,290,662 B1 | 9/2001 | Morris et al. | |
| 6,358,453 B1 | 3/2002 | Slemker et al. | |
| 6,368,357 B1 | 4/2002 | Schon et al. | |
| 6,387,065 B1 | 5/2002 | Tumey | |
| 6,423,017 B2 | 7/2002 | Brotz | |
| 6,494,852 B1 | 12/2002 | Barak et al. | |
| 6,500,210 B1 | 12/2002 | Sabolich et al. | |
| 6,508,842 B1 | 1/2003 | Caspers | |
| 6,544,202 B2 | 4/2003 | McEwen et al. | |
| 6,554,868 B1 | 4/2003 | Caspers | |
| 6,585,774 B2 * | 7/2003 | Dean et al. | 623/37 |
| 6,645,253 B2 | 11/2003 | Caspers | |
| 6,673,117 B1 | 1/2004 | Soss et al. | |
| 6,688,653 B1 | 2/2004 | Thrift et al. | |
| 6,726,726 B2 | 4/2004 | Caspers | |
| 6,761,742 B2 | 7/2004 | Caspers | |
| 6,926,742 B2 | 8/2005 | Caspers et al. | |
| 6,974,484 B2 | 12/2005 | Caspers | |
| 7,025,792 B2 | 4/2006 | Collier | |
| 7,025,793 B2 | 4/2006 | Egilsson | |
| 7,150,762 B2 | 12/2006 | Caspers | |
| 2001/0005798 A1 | 6/2001 | Caspers | |
| 2001/0016781 A1 | 8/2001 | Caspers | |
| 2002/0091449 A1 | 7/2002 | Caspers et al. | |
| 2004/0024322 A1 | 2/2004 | Caspers | |
| 2004/0059432 A1 | 3/2004 | Janusson et al. | |
| 2004/0098136 A1 | 5/2004 | Caspers | |
| 2004/0143345 A1 | 7/2004 | Caspers | |
| 2004/0163278 A1 | 8/2004 | Caspers | |
| 2004/0167638 A1 | 8/2004 | Caspers | |
| 2004/0181290 A1 | 9/2004 | Caspers | |
| 2004/0260402 A1 | 12/2004 | Baldini et al. | |
| 2004/0260403 A1 | 12/2004 | Patterson et al. | |
| 2006/0282174 A1 | 12/2006 | Haines | |
| 2007/0055383 A1 | 3/2007 | King | |
| 2007/0191965 A1 | 8/2007 | Colvin et al. | |

FOREIGN PATENT DOCUMENTS

| | | |
|---|---|---|
| BE | 675386 | 5/1966 |
| CA | 2098945 | 7/1997 |
| DE | 0745981 | 5/1944 |
| DE | 1566408 | 2/1971 |
| DE | 2712342 | 9/1977 |
| DE | 2729800 | 1/1979 |
| DE | 3221920 | 4/1983 |
| DE | 4039648 | 7/1992 |
| DE | 4217877 | 12/1992 |
| DE | 4321182 | 12/1994 |
| DE | 9418210 | 3/1995 |
| DE | 9419211 | 3/1995 |
| DE | 9417913 | 4/1995 |
| DE | 29905020 | 8/1999 |

| | | | |
|---|---|---|---|
| DE | 202006007460 | 9/2007 | |
| EP | 0019612 | 11/1980 | |
| EP | 0057839 | 8/1982 | |
| EP | 0086147 | 8/1983 | |
| EP | 0057838 | 3/1985 | |
| EP | 0261884 | 3/1988 | |
| EP | 0320170 | 6/1989 | |
| EP | 0363654 | 4/1990 | |
| EP | 0631765 | 1/1995 | |
| EP | 0650708 | 5/1995 | |
| EP | 0870485 | 10/1998 | |
| EP | 0 913 141 A2 * | 5/1999 | |
| EP | 1857081 | 11/2007 | |
| FR | 1135516 | 9/1960 | |
| FR | 1532625 | 7/1968 | |
| FR | 2420335 | 10/1979 | |
| FR | 2501999 | 9/1982 | |
| GB | 136504 | 1/1920 | |
| GB | 0267988 | 3/1927 | |
| GB | 1086560 | 10/1967 | |
| GB | 1191301 | 5/1970 | |
| GB | 1191633 | 5/1970 | |
| GB | 2069847 | 9/1981 | |
| GB | 2087727 | 6/1982 | |
| GB | 2149309 | 6/1985 | |
| SU | 0425629 | 4/1974 | |
| SU | 425629 * | 2/1975 | 623/37 |
| SU | 1771722 | 10/1992 | |
| SU | 1812981 | 4/1993 | |
| SU | 1812982 | 4/1993 | |
| SU | 1821177 | 6/1993 | |
| WO | WO 84/00881 | 3/1984 | |
| WO | WO 95/05792 | 3/1995 | |
| WO | WO 96/21405 | 7/1996 | |
| WO | WO 98/04218 | 2/1998 | |
| WO | WO 98/55055 | 12/1998 | |
| WO | WO 99/32056 | 7/1999 | |
| WO | WO 99/65434 | 12/1999 | |
| WO | WO 00/03665 | 1/2000 | |
| WO | WO 00/74611 | 12/2000 | |
| WO | WO 01/54631 | 8/2001 | |
| WO | WO 01/70147 | 9/2001 | |
| WO | WO 02/065958 | 8/2002 | |
| WO | WO 02/067825 | 9/2002 | |
| WO | WO 02/080813 | 10/2002 | |
| WO | WO 02/085264 | 10/2002 | |
| WO | WO 03/077797 | 9/2003 | |
| WO | WO 03/086245 | 10/2003 | |
| WO | WO 03/099173 | 12/2003 | |
| WO | WO 2005/039444 | 5/2005 | |

OTHER PUBLICATIONS

English translation of EP 0 913 141 A2.*

Article: *Vacuum-Assisted Closure: A New Method for Wound Control and Treatment: Clinical Experience* by L.C. Argenta, Michael J. Morykwas, PhD. Annals of Plastic Surgery vol. 38/No. 6/Jun. 1997, pp. 563-577.

Article: *The use of negative pressure to promote the healing of tissue defects: a clinical trial using the vacuum sealing technique* by T. Mullner, L.Mrkonjic, O.Kwasny, and V.Vecsei. British Journal of Plastic Surgery 1997, pp. 194-199.

Article: *Vacuum-Assisted Closure: A New Method for Wound Control and Treatment: Animal Studies and Basic Foundation* by M.J. Morykwas, L.C.Argenta, E.I.Shelton-Brown and W. McGuirt. Annals of Plastic Surgery vol. 38/No. 6/Jun. 1997 pp. 553-562.

Article: *Passive Vascular Exercises* by L.G. Herrmann and M.R. Reid. Archives of Surgery, vol. 29/No. 5, November, pp. 697-704.

Article: *Intermittent Pneumatic Compression on the Calf Improves Peripheral Circulation of the Leg* by H. Iwama, M.Suzuki, M.Hojo, M. Kaneda, and I.Akutsu. Journal of Critical Care, vol. 15, No. 1 (March), 2000: pp. 18-21.

Article: *Orthotic Management of the Neuropathic and Dysvascular Patient* by R.B.Chamers and N.Elftman. Orthotic Management of the Neuropathic and Dysvascular Patient pp. 427-453.

"Everyone talks about the weather, but nobody does anything about it", Gore-Tex web pages from http://www.gore-tex.com/goretex/index.html, printed Jul. 3, 2001, 2 pages.

Board, Wayne J. "Below-knee Amputee Residual Limb Responses to Vacuum-Assisted and Suction Socket Conditions", A Thesis Submitted to the Graduate Faculty of St. Cloud State University, Oct. 2000.

Gill Bike Gear & Apparel, web pages from http://www.gillbikegear.com/page-products-baselayer.htm, printed Jul. 3, 2001, 2 pages.

Harvey, Robert M. et al., "Research Forum—Methodology Measurements, Part II: Instrumentation and Apparatus", Journal of Prosthethics and Orthotics, vol. 8, No. 2, 1996 (pp. 50-64).

International Search Report issued in PCT/US01/09152, Dec. 18, 2001.

International Search Report issued in PCT/US02/28700, Sep. 12, 2003.

International Search Report issued in PCT/US2001/043874, Oct. 28, 2002.

International Search Report issued in PCT/US2001/043954, Oct. 28, 2002.

International Search Report issued in PCT/US2001/043955, Oct. 28, 2002.

International Search Report of EP 07 00 5857 mailed Oct. 12, 2007, 6 pages.

Mak, Arthur F. T. et al., "State-of-the-art research in lower-limb prosthetic biomechanics—socket interface", Journal of Rehabilitation Research & Development, vol. 38, No. 2, Mar./Apr. 2001, pp. 1-16.

Solomons, Organic Chemistry (6.sup.th ed,), John Wiley & Sons, Inc., New York, 1996 pp. 853-854.

"How Do They Work? Waterproof and Breathable. Why Both?" SealSkinz Waterproof and Breathable Socks and Gloves, Web Pages from www.sealskinz.com, Oct. 18, 2000, 4 pages.

Chambers, R.B. et al., "Orthotic Managment of the Neuropathic and Dysvascular Patient", Chapter 29, American Orthopaedic Surgeons Atlas of Orthotics and Assistive Devices, 3rd Edition, 1997, pp. 427-453.

Hermann, L.G. et al., "Passive Vascular Exercises", Archives of Surgery, vol. 29, No. 5, Nov. 1934, pp. 697-704.

Waterproof/Windproof/Breathable: How it Works, SympaTex Technologies GmbH Data Sheets, Jul. 9, 2001, 5 pages.

Beil, Tracy L. et al., "Comparison Of Interface pressures With Pin and Suction Suspension Systems", Journal of Rehabilitation Research & Development, vol. 41, No. 6A, Nov./Dec. 2004, pp. 821-828.

Beil, Tracy L., "Interface Pressures During Ambulation Using Suction and Vacuum-Assist Prosthetic Sockets", A Thesis Submitted to the Graduate Faculty of St. Cloud State University, Jul. 2001 (resubmitted with missing pages).

* cited by examiner

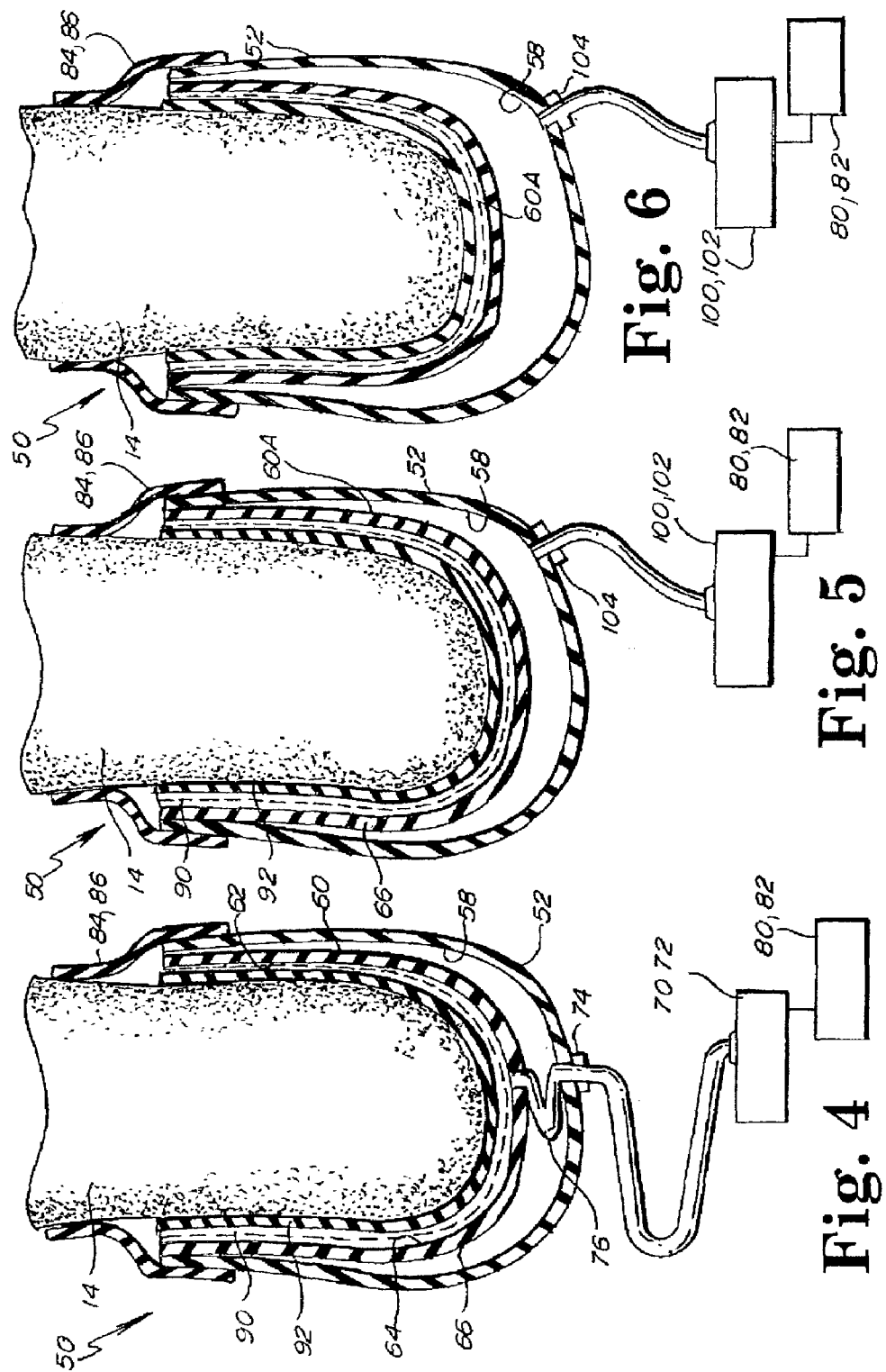

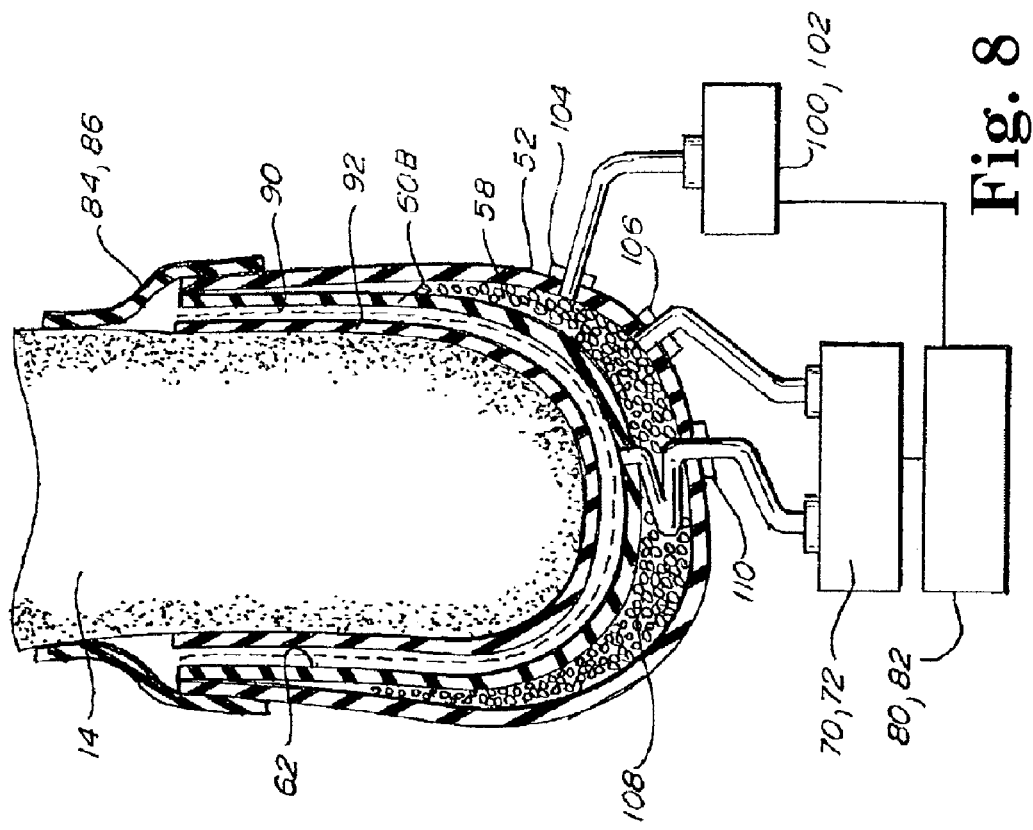
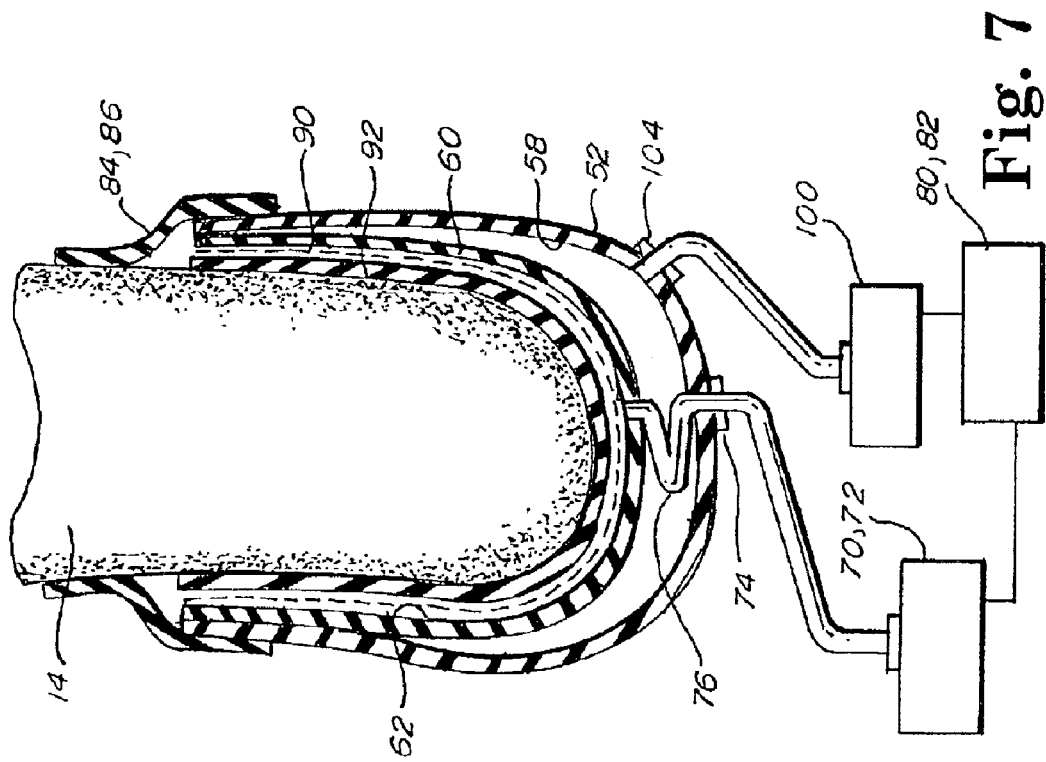

PULSATING PRESSURE CHAMBER AND METHOD FOR FLUID MANAGEMENT

This is a continuation-in-part of U.S. patent application Ser. No. 10/090,971, filed Mar. 4, 2002, and published as US 2002/0091449 A1 on Jul. 11, 2002, and issued as U.S. Pat. No. 6,926,742, which is a continuation-in-part of U.S. patent application Ser. No. 09/785,714, filed on Feb. 16, 2001 and published as U.S. 2001/0005798 on Jun. 28, 2001, and issued as U.S. Pat. No. 6,726,726, which is a continuation-in-part of U.S. patent application Ser. No. 09/492,406, filed on Jan. 27, 2000, and issued as U.S. Pat. No. 6,508,842 B1, which is a continuation-in-part of U.S. patent application Ser. No. 09/325,297, filed on Jun. 3, 1999, now abandoned. This application also claims the benefit of U.S. Provisional Application Ser. No. 60/383,159, filed on May 23, 2002 and entitled PULSATING BASIC PRESSURE CHAMBER FOR ENHANCED BLOOD FLOW.

FIELD OF THE INVENTION

This invention relates to pressure chambers used to enhance blood flow in body parts and manage fluid flow and accumulation in those body parts. In particular, pressure chambers formed as artificial limbs for amputees.

BACKGROUND OF THE INVENTION

An amputee is a person who has lost part of an extremity or limb such as a leg or arm which commonly may be termed as a residual limb. Residual limbs come in various sizes and shapes with respect to the stump. That is, most new amputations are either slightly bulbous or cylindrical in shape while older amputations that may have had a lot of atrophy are generally more conical in shape. Residual limbs may further be characterized by their various individual problems or configurations including the volume and shape of a stump and possible scar, skin graft, bony prominence, uneven limb volume, neuroma, pain, edema or soft tissue configurations.

Referring to FIG. 1, a below the knee residual limb or residuum 10 is shown and described as a leg 12 having been severed below the knee terminating in a stump 14. In this case, the residual limb 10 includes soft tissue as well as the femur 16, knee joint 18, and severed tibia 20 and fibula 22. Along these bone structures surrounded by soft tissue are nerve bundles and vascular routes which must be protected against external pressure to avoid neuromas, numbness and discomfort as well as other kinds of problems. A below the knee residual limb 10 has its stump 14 generally characterized as being a more bony structure while an above the knee residual limb may be characterized as including more soft tissue as well as the vascular routes and nerve bundles.

Referring to FIG. 2, amputees who have lost a part of their arm 26, which terminates in a stump 28 also may be characterized as having vascular routes, nerve bundles as well as soft and bony tissues. The residual limb 10 includes the humerus bone 30 which extends from below the shoulder to the elbow from which the radius 34 and ulna 36 bones may pivotally extend to the point of severance. Along the humerus bone 30 are the biceps muscle 38 and the triceps muscle 40 which still yet may be connected to the radius 34 and the ulna, 36, respectively.

In some respects, the residual limb amputee that has a severed arm 26 does not have the pressure bearing considerations for an artificial limb but rather is concerned with having an artificial limb that is articulable to offer functions typical of a full arm, such as bending at the elbow and grasping capabilities. An individual who has a paralyzed limb would also have similar considerations wherein he or she would desire the paralyzed limb to having some degree of mobility and thus functionality.

Historically, artificial limbs typically used by a leg amputee were for the most part all made out of wood such as an Upland Willow. The limbs were hand carved with sockets for receiving the stump of the residual limb. Below the socket would be the shin portion with the foot below the shin. These wooden artificial limbs were covered with rawhide which often were painted. The sockets of most wood limbs were hollow as the limbs were typically supported in the artificial limb by the circumferential tissue adjacent the stump rather than at the distal end of the stump.

Some artificial limbs in Europe were also made from forged pieces of metal that were hollow. Fiber artificial limbs were also used which were stretched around a mold after which they were permitted to dry and cure. Again, these artificial limbs were hollow and pretty much supported the residual limb about the circumferential tissue adjacent the stump.

All of these various artificial limbs have sockets to put the amputee's stump therein. There are generally two categories of sockets. There are hard sockets wherein the stump goes right into the socket actually touching the socket wall without any type of liner or stump sock. Another category of sockets is a socket that utilizes a liner or insert. Both categories of sockets typically were open-ended sockets where they had a hollow chamber in the bottom and no portion of the socket touched the distal end of the stump. So, the stump was supported about its circumferential sides as it fits against the inside wall of the sockets.

These types of sockets caused a lot of shear force on the stump and had pressure or restriction problems on the nerve bundles and vascular flow of fluid by way of the circumferential pressure effect of the socket on the limb. This pressure effect could cause a swelling into the end of the socket where an amputee may develop severe edema and draining nodules at the end of the stump.

With time, prosthetists learned that by filling in the socket's hollow chamber and encouraging a more total contact with the stump and the socket, the swelling and edema problems could be eliminated. However, the problematic tissue configurations, such as bony prominences, required special consideration such as the addition of soft or pliable materials to be put into the socket.

Today, most artificial limbs are constructed from plastics such as polyester resins, acrylic resins, polypropylenes and polyethylenes, which are perhaps laminated over a nylon stockinette which also may be impregnated by the various resins.

In the past, most artificial limbs were suspended from the amputee's body by some form of pulley, belt or strap suspension often used with various harnesses and perhaps leather lacers or lacings. Another method of suspending artificial limbs is known as the wedge suspension wherein an actual wedge is built into the socket which is more closed at its top opening. The wedge in the socket cups the medial femoral condyle or knuckle at the abductor tubical. Yet another form of suspension is referred to as the shuttle system or a mechanical hookup or linkup wherein a thin suction liner is donned over the stump that has a docking device on the distal end which mechanically links up with its cooperative part in the bottom of the socket chamber. Sleeve suspensions were also used wherein the amputee may use a latex rubber tube which forms into a rubber-like sleeve which would be rolled on over both the top of the artificial limb and onto the amputee's thigh. The sleeve suspensions have been used in combination with other forms of suspensions techniques.

Both the use of a positive pressure system and the use of a negative pressure system (or hypobaric closed chamber) have been utilized in the field of prosthetics. At one time, for pressure systems "inflatable inner tubes" were used to fit into sockets. Presently, there are pneumatic "bags" which are strategically placed over what people consider to be good weight-bearing areas to increase pressure to help accommodate for volume changes within the socket.

The problem with this is that it is a very specific pressure and creates atrophy and loss of tissue dramatically over these high pressure areas. None of these systems employs positive pressure distributed over the total or substantially total contact area between the residual limb and the artificial limb socket to accommodate volume changes within the socket.

The negative pressure aspects have been utilized for a closed chamber in that a socket is donned by pulling in with a sock, pulling the sock out of the socket and then closing the opening with a valve. This creates a seal at the bottom and the stump is held into the socket by the hypobaric seal.

The older systems were initially started in Germany. They were an open-ended socket, meaning there was an air chamber in the bottom of the socket. This did not work particularly well because it would cause swelling of the residual limb into the chamber created by the negative draw of suspending the weight of the leg and being under a confined area. This would lead to significant edema which would be severe enough to cause stump breakdown and drainage.

It was later discovered in America that total or substantially total contact was essential between the residual limb and the socket and once you had total or substantially total contact the weight was distributed evenly or the suspension was distributed over the whole surface of the limb rather than just over the open chamber portion of the socket.

The human body as a whole is under approximately one atmosphere of pressure at sea level. It keeps and maintains a normal fluid system throughout the body. When an amputee dons a prosthesis and begins taking the pressures of transmitting the weight of the body through the surface area of the residual limb to the bone, there is increased pressure on the residual limb equal to one atmosphere plus whatever additional pressures are created by weight bearing. This increased pressure or positive pressure causes the eventual loss of fluids within the residual limb to the larger portion of the body which is under less pressure. This loss of fluids causes the volume of the residual limb to decrease during the day. It varies from amputee to amputee, but the more "fleshy" and the softer the residual limb, the more volume fluctuation there will generally be. The greater the weight and the smaller the surface area, the greater the pressures will be and the more "swings" there will be in fluid volume. In the past, the amputee had to compensate for this volume decrease by removing the artificial limb and donning additional stump socks to make up for the decreased residual limb volume.

U.S. Pat. No. 5,888,230 discloses the use of a vacuum pump connected between the limb and a liner. However, this invention is essentially inoperable because the liner will conform to the stump at all times, by an interference fit, so that there is no space between the residual limb and the liner against which to draw a vacuum. In any case, the patent does not disclose application of vacuum to, or create negative pressure within, the socket cavity in such a manner as to draw the residual limb firmly and totally against the interior of the socket. Instead, the patent discloses the use of shims between the liner and the socket. Without total contact between the residual limb and the socket, the limb may swell into the space between the limb and the socket. Also, the patent does not disclose the use of vacuum to prevent reduction in volume of the artificial limb due to weight-bearing pressures.

While some of these devices addressed some of the problems associated with prosthetics, none of the artificial limbs, liners and socket, individually or in combination, offered a prosthesis that presented a total contact relationship with the residual limb; absorbed and dissipated shear, shock and mechanical forces transmitted to the limb tissues by the artificial limb; controlled residual limb volume; and used negative pressure as a locking device to hold the residual limb into the socket.

There was a need for an improved artificial limb that will offer a total or substantially total contact relationship with the residual limb; absorb and dissipate shock, mechanical and shear forces typically associated with ambulation, twisting and turning and weight bearing with an artificial limb; control residual limb volume by way of even force distribution; use negative pressure as a locking device to hold the residual limb into the socket without causing swelling of the residual limb into the socket; and control residual limb volume changes by a negative pressure system. Ideally, the pressure control system should be automatically regulated.

U.S. Pat. No. 5,549,709 discloses several embodiments of an artificial limb. However, all of these embodiments require two sockets: an outer socket and an inner socket. Applicant has found that the present invention offers improved performance without the requirement for two sockets. A single socket can work equally well or better than two sockets. Also, this patent does not disclose a mechanism for maintaining vacuum or a negative pressure in the presence of air leakage into the socket.

It has been found that it is difficult to maintain a perfect, airtight seal between the residual limb and the sockets disclosed in U.S. Pat. No. 5,549,709, with the result that slow air leakage into the sockets diminishes the vacuum in the sockets. With the reduction in vacuum, the beneficial effects of the vacuum also slowly diminish. Consequently, there was a need for our apparatus and/or method for maintaining the vacuum in the socket cavity in the presence of some air leakage past the seal.

As mentioned above, fluid management within a residual limb becomes a problem during the wearing of a prosthetic device by an amputee. Loss of fluid from the residual limb can occur during the course of a day or over a longer period of time, causing fit problems with the prosthetic device. In addition, prosthetic devices may also cause swelling and edema problems in residual limbs due to pooling of fluid. The effects of pressure, both positive and negative, within the prosthesis may compound these potential problems. Often, amputees also encounter vascular flow problems in the residual limb resulting in additional amputation of limb material. Sometimes these vascular problems are the reason for the amputation in the first place. Such vascular problems may cause wounds within the residual limb, or may inhibit proper healing of wounds within the residual limb obtained for any reason.

The use of positive pressure, negative pressure, and alternating positive and negative pressure on a body part to promote wound healing and to enhance blood flow has been shown previously. Large pressure chambers that receive a body part and apply positive pressure to the part have also been previously shown.

For amputees, management of fluid within a residual limb is important for fit and comfort reasons. In addition, management of fluid in a body tissue is also important for proper vascular flow and wound reduction and/or healing. Among other things, there is a need for an apparatus to apply alternating positive and negative pressure to a body part, such as a residual limb, wherein the apparatus is provided in conjunction with a prosthetic device and is programmably controlled in order to control the amplitude and/or frequency of the changes in pressure and improve the therapeutic effect.

SUMMARY OF THE INVENTION

The present invention is directed to an apparatus for enhancing blood flow to a body part through the use of alternating positive and negative pressure. In particular, the invention relates to such an apparatus programmably controlled in order to control the amplitude and/or frequency of the changes in pressure. The present invention provides an apparatus for securing a prosthesis to the residuum of a limb of an amputee and for providing pressure therapy to the residuum. The apparatus includes a socket shaped to receive a residuum of a limb of an amputee and is configured to connect to a prosthetic limb. The socket forms a chamber between the socket and the residuum when the socket receives the residuum. The apparatus also includes a pressure control device operably connected to the chamber and capable of creating a positive pressure and a negative pressure within the chamber to provide pressure therapy to the residuum. The pressure control device adjusts pressure within the chamber based on manual inputs, sensory inputs or other information, and may affect securement of the socket to residuum.

The present invention also provides a method for securing a prosthesis to the residuum of a limb of an amputee and for providing pressure therapy to the residuum when the amputee is using a prosthetic limb. The method includes the step of placing a socket onto a residuum of a limb of an amputee. The socket is shaped to receive the residuum and is configured to connect to a prosthetic limb, with the socket forming a chamber between the socket and the residuum when the socket receives the residuum. The method also includes the step of controlling a change between positive and negative pressure within the chamber to provide pressure therapy to the residuum.

A principal object and advantage of the present invention is that it increases blood flow to a body part.

Another principal object and advantage of the present invention is that it includes a computer that can regulate the change in amplitude and frequency in the positive and negative pressure to produce a wave of any shape.

BRIEF DESCRIPTION OF THE SEVERAL VIEWS OF THE DRAWINGS

FIG. 4 is a cross-section of the artificial limb in FIG. 3, which is a first embodiment of the artificial limb;

FIG. 5 is a cross-section of the artificial limb similar to FIG. 4, showing a second embodiment of the artificial limb;

FIG. 6 is the same as FIG. 5, but showing compression of the inner socket under the influence of positive air pressure;

FIG. 7 is a cross-section of the artificial limb showing a third embodiment of the artificial limb;

FIG. 8 is a cross-section of the artificial limb showing a fourth embodiment of the artificial limb;

DETAILED DESCRIPTION OF THE INVENTION

With reference to the attached Figures, it is to be understood that like components are labeled with like numerals throughout the several Figures. The present invention includes an apparatus for providing pressure therapy as alternating positive and negative pressure in an enclosure, such as an artificial limb or prosthesis, surrounding a portion of a body, such as a residual limb, for the purpose of improving blood flow and managing fluid within the residual limb.

The drawings show a number of different embodiments of an apparatus and method for managing the volume of fluid in a residual limb joined to an artificial limb, by applying a vacuum source to the artificial limb cavity or chamber. It will be seen that application of the vacuum to the cavity can draw the residual limb (which may be encased in a liner) firmly and totally against the socket, thereby preventing or reducing swelling of the residual limb into the socket, because there is little or no open chamber into which the residual limb may be drawn by the vacuum. Importantly, application of the vacuum to the cavity also opposes the loss of fluids from the residual limb due to weight-bearing pressures.

Figure 1:
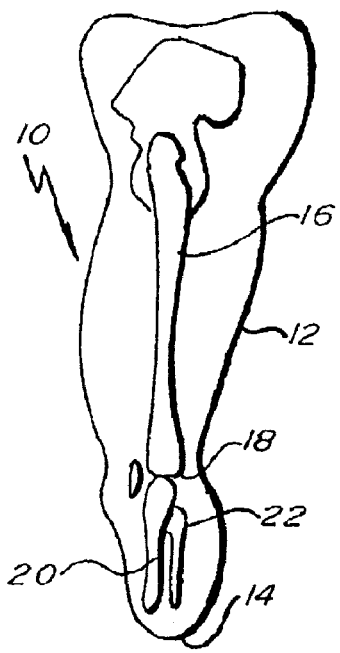
FIG. 1 is a side elevational view of the tissue and skeletal structure of an amputee's residual limb.
Figure 2:
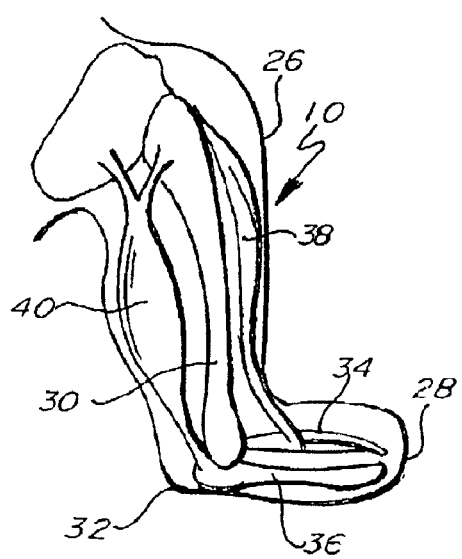
FIG. 2 is a side elevational view of a residual limb in the form of an amputated arm showing the skeletal and muscular structure of the residual limb.
Figure 9:
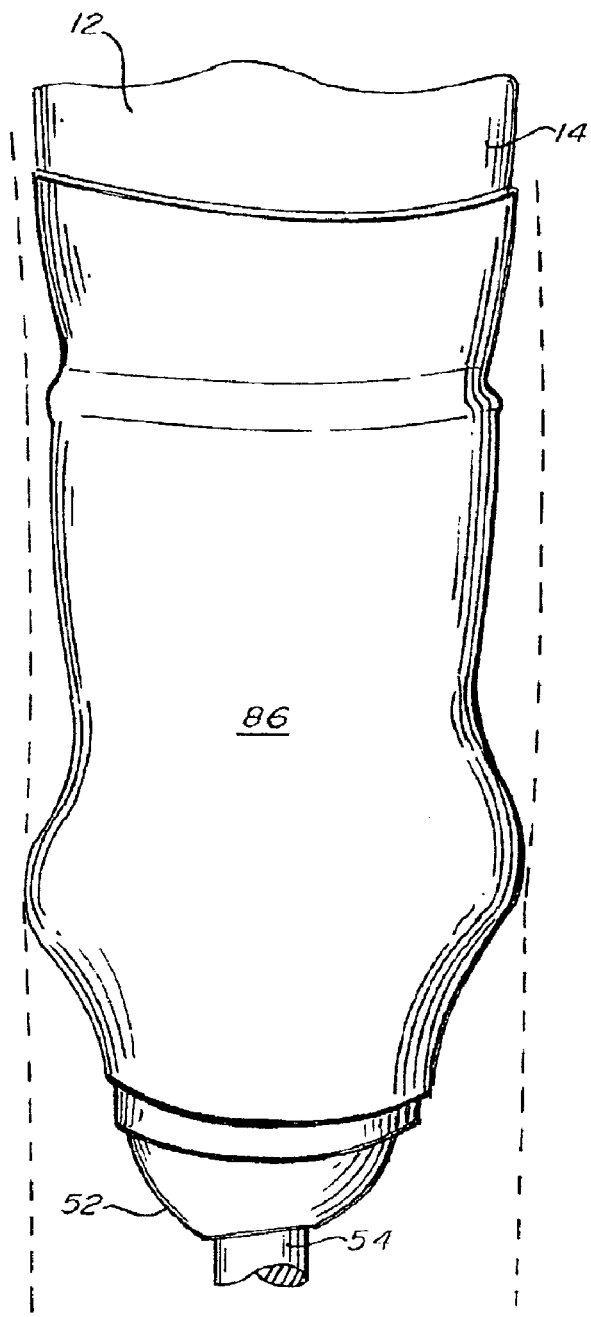
FIG. 9 is an elevational view of the polyurethane sleeve and second stretchable nylon sleeve rolled over the socket and residual limb with clothing shown in broken outline.
Figure 3:
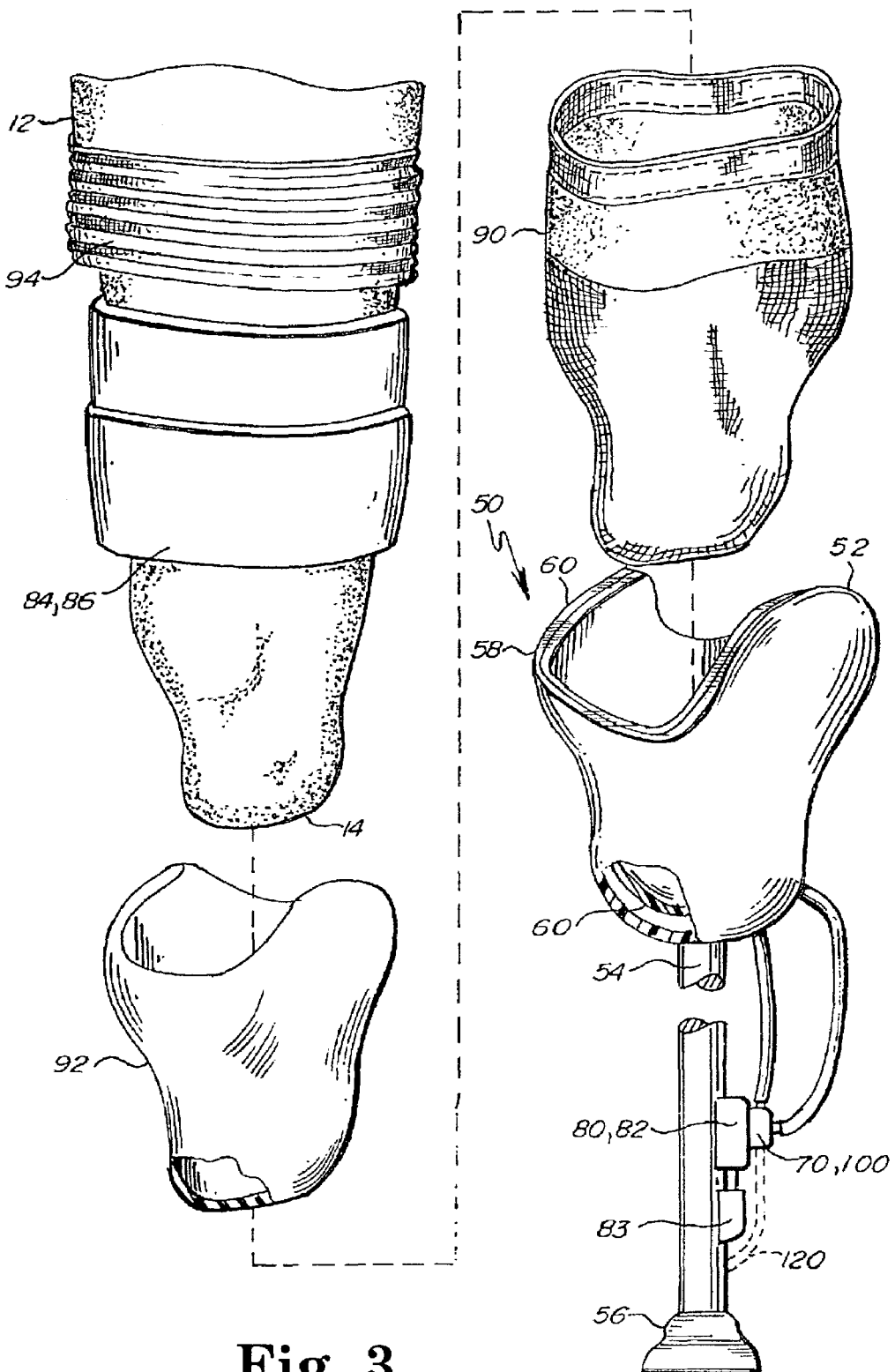
FIG. 3 is an exploded elevational view of the residual limb donning the polyurethane sleeve, stretchable nylon sleeve, liner, nylon sheath and socket of an artificial limb.

FIGS. 3 and 4 show one embodiment of the apparatus 50 of the present invention. The artificial limb 50 includes an outer socket 52, shin 54, and foot 56. The outer socket 52 has a volume and shape to receive a substantial portion of the residual limb 14 with a space 58 or chamber therebetween.

The apparatus 50 further includes a flexible inner socket 60 with a cavity 62 with a volume and shape for receiving a substantial portion of the residual limb 14 and fitting in the space 58 between the outer socket 52 and the residual limb 14. The inner socket 60 has an inner surface 64 opposing the residual limb 14 and an outer surface 66 opposing the outer socket 52.

A vacuum source 70 may conveniently be attached to or within the shin or pylon 54. The vacuum source 70 may preferably be a mechanical or motor-driven pump 72. The vacuum source 70 may be connected to a power source 83, which may be a battery or a weight-bearing powered generator could be used.

A vacuum valve 74 is suitably connected to the vacuum source 70. The vacuum valve 74 may preferably be disposed on the outer socket 52. A vacuum tube 76 connects the vacuum valve 74 to the cavity 62 or chamber. It will be seen that the vacuum source will cause the residual limb 14 to be drawn into firm contact with or in closer proximity to the inner surface 64 of the inner socket 60.

The artificial limb 50 also includes a regulator means 80 for controlling the vacuum source 70. Preferably, the regulator means 80 may be a digital computer 82. Alternately, the regulator means 80 may be a vacuum regulator. The regulator means 80 is connected to a power source 83, which may be a battery.

A seal means 84 makes an airtight or nearly airtight seal between the residual limb 14 and the outer socket 52. Preferably, the seal means 84 is a nonfoamed, nonporous polyurethane suspension sleeve 86 which rolls over and covers the outer socket 52 and a portion of the residual limb 14. Alternatively, the seal means 84 may be any type of seal which is airtight or nearly airtight.

The artificial limb 50 may also include a thin sheath 90 between the residual limb 14 and the inner surface 64 of the inner socket 60. As vacuum is applied to the cavity 62, the sheath 90 will allow the vacuum to be relatively evenly applied throughout the cavity 62. Without the sheath 90, the residual limb 14 might "tack up" against the inner surface 64 and form a seal which might prevent even application of the vacuum to the cavity 62. The sheath 90 may also be used to assist the amputee into a smooth and easy fitting into the inner socket 60. The sheath 90 is preferably made of thin knitted nylon.

The apparatus 50 may also include a nonfoamed, nonporous polyurethane liner 92 receiving the residual limb 14 and disposed between the sheath 90 and the residual limb 14. The liner 92 provides a total or substantially total contact hypobaric suction, force-distributed socket liner. The liner 92 readily tacks up to the skin of the residual limb 14 and provides total contact with the limb 14. The liner 92 absorbs and dissipates shock, mechanical and shear forces typically associated with ambulation.

The artificial limb 50 may also include a stretchable nylon second sleeve 94 for rolling over and covering the suspension sleeve 86 to prevent clothing from sticking to and catching the suspension sleeve 86.

Referring to FIG. 3, the polyurethane tubular sleeve 86 may be used alone or in combination with the polyurethane liner 92 together with the optional nylon sheath 90 and second stretchable nylon sleeve 94.

More specifically, the amputee can take the stretchable nylon second sleeve 94, suitably made of a spandex-like material and roll it up over the stump 14 to the upper portions of the residual limb suitably as the thigh of a leg 12. Next, the polyurethane sleeve 86 can also be rolled upwardly over the residual limb 10. Thereafter, the liner 92 is optionally donned.

Next, the amputee may optionally utilize the nylon sheath 90 which is suitably of a non-stretching, thin, friction reducing nylon. As stated, this sheath 90 optionally may be used to assist the amputee into a smooth and easy fitting into the inner socket 60. Alternatively, the sheath 90 may be avoided and the liner 92 simply inserted into the inner socket 60 of the artificial limb 50.

Next, the amputee simply grasps the rolled over portion of the polyurethane sleeve 86 and rolls it over a substantial portion of the outer socket 52. The sleeve 86 makes an airtight seal between the residual limb 14 and the outer socket 52.

As can be appreciated, the polyurethane sleeve 86 is tacky. Consequently, the stretchable nylon second sleeve 94 may be utilized and rolled over the polyurethane sleeve 86.

The amputee then sets the regulator means 80 to cause the vacuum source 70 to apply vacuum through the vacuum valve 74 and vacuum tube 76 to the cavity 62. Enough vacuum is applied to cause the residual limb (with optional coverings) to be drawn firmly against the inner surface 64 of the inner socket 60, which is flexible. The vacuum source 70 may preferably maintain a vacuum in the range of 0 to 25 inches of mercury (ideally ten to twenty-five inches).

It will be seen that the vacuum within the inner socket 60 will cause the artificial limb 50 to be suspended from the residual limb 14. The vacuum will lock the residual limb 14 into the inner socket 60 without causing swelling of the residual limb into the inner socket 60, because of the total contact of the residual limb 14 with the inner socket 60. That is, there is no open chamber between the residual limb 14 and the inner socket 60 which would draw on the residual limb.

As the volume of the residual limb 14 decreases during the day due to weight-bearing pressures, the regulator means 80 may appropriately adjust the vacuum source 70 to draw the residual limb 14 more firmly against the inner socket 60 and thus compensate for the loss of residual limb volume. The vacuum may also partially or completely oppose the loss of fluids from the residual limb caused by weight-bearing pressures.

FIGS. 3 and 4, as discussed above, show a number of features and components. One or more of these features and components can be excluded or replaced. The same is true of the embodiments shown in the other figures, as set forth below.

A second embodiment of the apparatus 50 is shown in FIGS. 5 and 6. The second embodiment of the apparatus 50 is as described above, with the exception that the inner socket 60A is compressible as well as being flexible. Instead of a vacuum source, the second embodiment has a positive air pressure source 100, which may preferably be a motor-driven pump 102. The regulator or regulator means 80, which may be a computer 82, controls the positive air pressure source 100. The regulator means and positive air pressure source 100 are connected to a power source 83, which may be a battery. A positive pressure valve 104 connects the space 58 to the positive air pressure source 100, for compressing the inner socket 60A as the volume of the residual limb decreases.

It will be seen that as the volume of the residual limb 14 decreases during the day due to weight-bearing pressures, the regulator means 80 may control the positive air pressure source 100 to cause air pressure to compress the inner socket 60A to compensate for the decreased volume of the residual limb, as shown in FIG. 6.

A third embodiment of the artificial limb 50 is shown in FIG. 7. The third embodiment can be considered a combination of the first and second embodiments described above.

A device, such as a mechanical motor-driven pump 72 may act as both the vacuum source 70 and the positive air pressure source 100. The regulator means 80, vacuum source 70 and positive air pressure source 100 are connected to a power source (not shown), which may be a battery.

The vacuum source 70, under control of the regulator means 80, will compensate for reduced residual limb volume up to a certain point. From that point on, the regulator means 80 will cause the positive air pressure source 100 to further compensate for reduced residual limb volume as described above. The third embodiment thus uses both vacuum and positive air pressure working together to lock the residual limb 14 into the inner socket 60 and reduce socket volume to compensate for fluid loss in the residual limb 14. The exact point at which the changeover is made between vacuum compensation and positive air pressure compensation can be controlled by the regulator means 80, which as described may be a computer appropriately programmed for the socket environment.

A fourth embodiment of the apparatus 50 is shown in FIG. 8. The fourth embodiment is like the first embodiment, but includes two vacuum valves: a first vacuum valve 106 and a second vacuum valve 110, both connected to the vacuum source 70. The first vacuum valve 106 connects the vacuum source 70 to the space 58. The space 58 contains a semi-compressible material 108, such as polystyrene beads, as disclosed in U.S. Pat. No. 4,828,325, herein incorporated by reference.

To don the artificial limb 50, the amputee proceeds as described above. After inserting the residual limb 14 (with optional coverings) into the inner socket 60B, which is both compressible and expandable, and rolling the suspension sleeve 86 over the outer socket 52, the amputee activates the regulator means 80, causing the vacuum source 70 to apply a vacuum to the space 58. This causes the material 108 to lock mechanically together into a rigid mass, conforming to the shape of the residual limb 14. The inner socket 60B may expand slightly under the weight of the residual limb 14 and under the influence of vacuum.

It will be seen that the semi-compressible molding material 108 can be molded to the contours of the residual limb 14 without using a custom-building process to produce a custom socket. The outer socket 52 may appropriately occur in standard sizes, such as small, medium, and large. The inner socket 60B may also occur in standard sizes such as small, medium, and large. Adaptation of the inner socket 60B to the contours of the residual limb 14 occurs through solidifying the material 108 under the influence of vacuum.

The second vacuum valve 110 connects the vacuum source 70 to the cavity 62 as previously described, for locking the residual limb 14 into the inner socket 60B.

The fourth embodiment may also include a positive air pressure source 100 as previously described, to adjust the size of the inner socket 60B to compensate for decreased residual limb volume.

The fourth embodiment may also include a thin sheath 90, liner 92, and second sleeve 94, as previously described.

The positive air pressure source 100 may also be used for shock absorption and a dynamic response in the ankle and foot sections of the artificial limb 50, by means of a connection 120.

Figure 10:
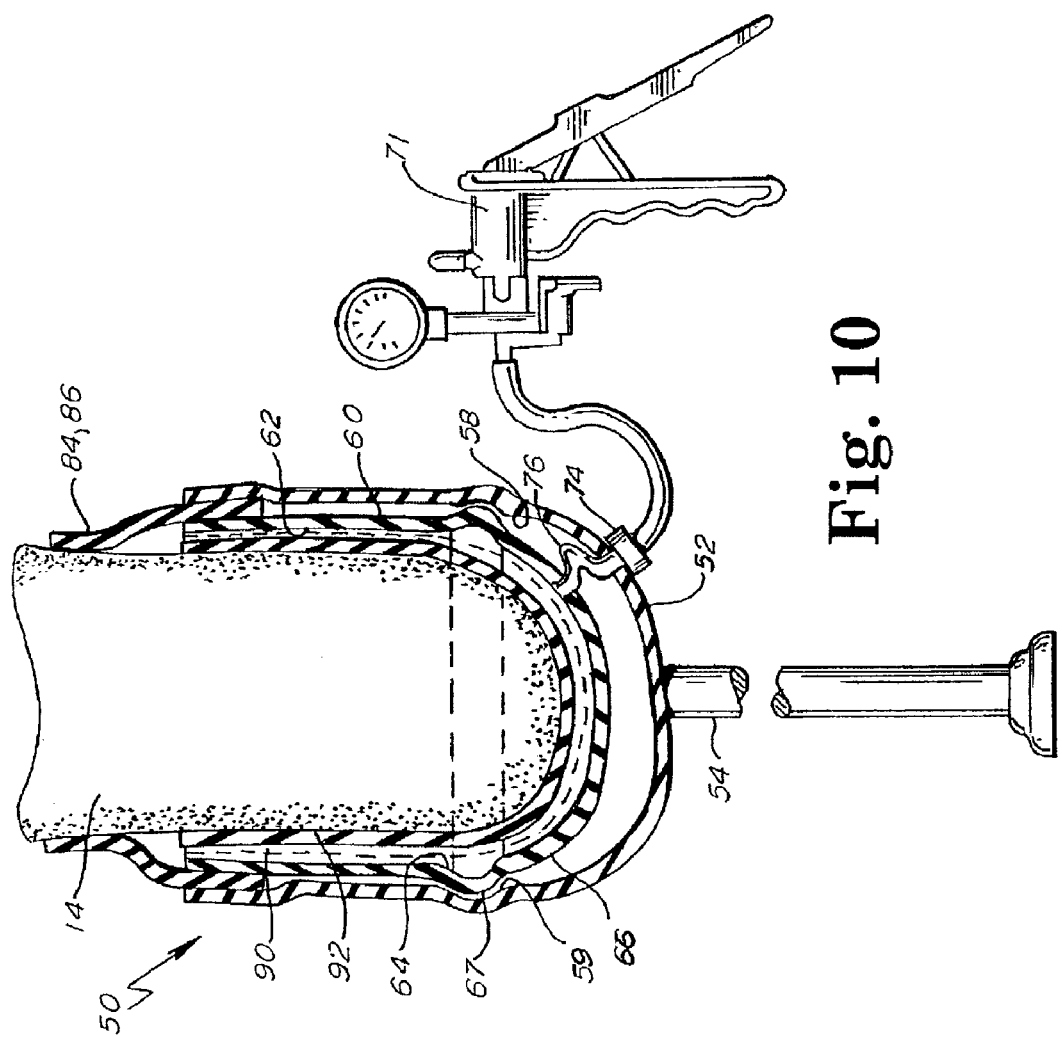
FIG. 10 is a cross-section of the artificial limb showing a fifth embodiment of the artificial limb.

A fifth embodiment of the artificial limb 50 is shown in FIG. 10. This embodiment is the same as the first embodiment shown in FIG. 4, with some changes. First, vacuum source 71 may be a hand-operated vacuum pump 71 which may remove air from the cavity 62 down to approximately 10-25 inches of mercury. A suitable hand-operated vacuum pump is marketed under the trademark MITY VAC II by Neward Enterprises, Inc. of Cucamonga, Calif. Instead of a hand-powered vacuum source, one could be foot powered or powered by movement of the prosthesis, such as at a knee joint.

The fifth embodiment also includes the seal or seal means 84 which preferably consists of a non-foamed, nonporous polyurethane suspension sleeve 86 for rolling over and covering a portion of the residual limb 14. A portion of the seal means 86 is adapted to be disposed between the outer socket 52 and the inner socket 60. The sleeve may be made, for example, of any of a variety of air-impervious elastomers.

The fifth embodiment, shown in FIG. 10 also includes a mechanical interlock 67, 59 for interlocking the inner socket 62 with the outer socket 52. Preferably, the mechanical interlock consists of a first detent 67 in the inner socket 62 and a second detent 59 in the outer socket 52. The first detent 67 engages the second detent 59 to lock the inner socket 60 into the outer socket 52.

Figure 12:
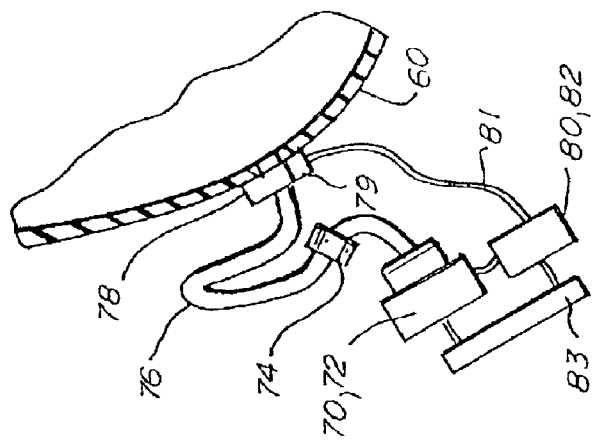
FIG. 12 is a detailed view of the vacuum mechanism in FIG. 11.
Figure 11:
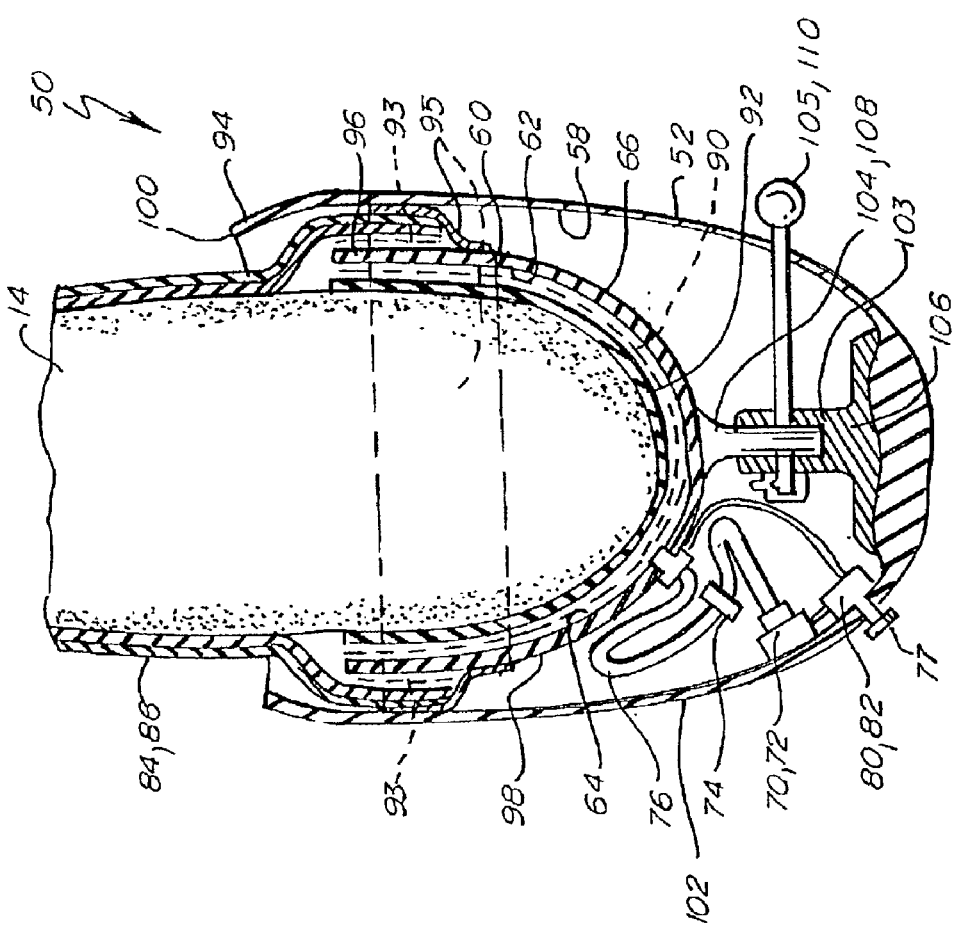
FIG. 11 is a cross-section of the artificial limb showing a sixth embodiment of the artificial limb.

A sixth embodiment of the apparatus of the present invention is shown in FIGS. 11 and 12. The sixth embodiment can be considered a variation of the first embodiment shown in FIG. 4.

First, the inner socket is specifically intended to be removable from the outer socket. To provide a positive mechanical connection between the inner socket and outer socket and yet allow the inner socket to be easily removed, the sixth embodiment includes a mechanical interlock 103 engaging the inner socket 60 and the outer socket 52. Preferably, the mechanical interlock may be an extension 104 which is attached to the inner socket 60 and a docking device 106 attached to the outer socket 52 and receiving the extension 104, and a locking mechanism 105 engaging the extension 104 and the docking device 106.

The extension may be any sort of protrusion from the inner socket, such as a bulge or tab. Preferably, the extension 104 comprises a shuttle pin 108.

The locking mechanism may be any sort of member which engages both the extension 104 and the docking device 106, such as a screw, wire, or pin. Preferably, the locking mechanism 105 comprises a second pin 110 which extends outside the outer socket 52 as to be accessible.

Second, the sixth embodiment includes two thin sheaths, rather than one. A first inner sheath 90 may preferably be disposed between the residual limb 14 and the inner surface 64 of the inner socket 60. As vacuum is applied to the cavity 62, the inner sheath 90 will allow the vacuum to be evenly applied throughout the cavity 62. Without the inner sheath 90, the residual limb 14 might "tack up" against the inner surface 64 and form a seal which might prevent even application of the vacuum to the cavity 62. The inner sheath 90 may also be used to assist the amputee into a smooth and easy fitting into the inner socket 60.

An outer sheath 93 is preferably disposed between the suspension sleeve 86 and the inner socket 60, thereby preventing the suspension sleeve 86 from tacking to the inner socket 60. Such tacking would cause friction between the inner socket 60 and the sleeve 86 which would cause the sleeve to wear out. Such tacking might also cause restrictions in the movement of the residual limb. The outer sheath 93 also protects the suspension sleeve 86 from being damaged by friction with the inner socket 60.

The sixth embodiment also preferably includes an adhesive pressure tape 95 adapted to cover the outer sheath 93, suspension sleeve 86, and the second sleeve 94 and sealing the outer sheath 93, suspension sleeve 86, and the second sleeve 94 to the inner socket 60. The tape 95 locks all of these layers to the inner socket so that they do not come loose during movement. Hook-and-loop type connectors could also be used in place of or in conjunction with the tape 95.

In the sixth embodiment, the suspension sleeve 86 goes between the inner socket 60 and the outer socket 52, so that the sleeve 86 is protected from damage.

In the sixth embodiment, the inner socket 60 has a rigid lower portion 98 and a substantially flexible upper portion 96. The rigid lower portion assists in weight-bearing while the substantially flexible upper portion allows for movement of the residual limb 14. As the knee is bent from straight to flexed, the width of the knee changes rather significantly and in a hard, non-flexible socket brim, there can be excessive pressure on the residual limb 14. The substantially flexible upper portion 96 makes the artificial limb 50 more comfortable and more adaptive to these changes. For the same reason, the outer socket 52 has a rigid lower portion 102 and a substantially flexible upper portion 100.

Preferably, the top edge of the inner socket 60 is below the top edge of the outer socket 52 so that the sleeve 86 is protected from impact. Preferably, the top edge of the inner socket 60 may be {fraction (3/16)} inch below the top edge of the outer socket 52.

The sixth embodiment includes extensive modifications to the vacuum system.

First, a vacuum fitting 78 has been added to the inner socket 60 to attach the vacuum tube 76. The vacuum fitting 78 allows the attachment of a vacuum sensor 79 adapted to sense the amount of vacuum in the cavity 62 and a sensor lead 81 is attached to the sensor 79 connecting the sensor 79 to the regulator means 80, thus conveying the sensed vacuum to the regulator means 80.

A vacuum valve 74 is placed between the cavity 62 and the vacuum source 70 to maintain vacuum in the cavity 62. Typically, the vacuum valve 74 is a one-way valve or non-return valve.

In the sixth embodiment, the vacuum source 70, vacuum tube 76, vacuum valve 74, regulator means 80, and power source 83 are all attached to the outer socket 52 in the space 58 between the outer socket 52 and inner socket 60. In this way, these delicate components are protected against being damaged by impact. Because of the placement of the regulator means 80 within the outer socket 52, a vacuum control 77 is provided extending outside the outer socket 52 to allow manual control of the regulator means 80.

The amputee dons the sixth embodiment in a manner similar to that earlier described, with some modifications. First, the outer sheath 93 is put on the residual limb 14 after rolling the suspension sleeve 86 upward over the residual limb and before donning the liner 92. After donning the inner sheath 90 over the liner 92, the amputee inserts the residual limb 14 into the inner socket 60. Next, the outer sheath 93, suspension sleeve 86, and second sleeve 94 are rolled down over the inner socket 60, and the adhesive pressure tape 95 is applied. Next, the wearer sets the regulator means 80 to an appropriate vacuum level by means of the vacuum control 77, and connects the vacuum tube 76 to the vacuum fitting 78. The inner socket 60 is then placed within the outer socket 52 so that the shuttle pin 108 engages the docking device 106 and the locking pin 110 is set to engage the shuttle pin 108 and the docking device 106, providing a positive mechanical interlock.

Figure 13:
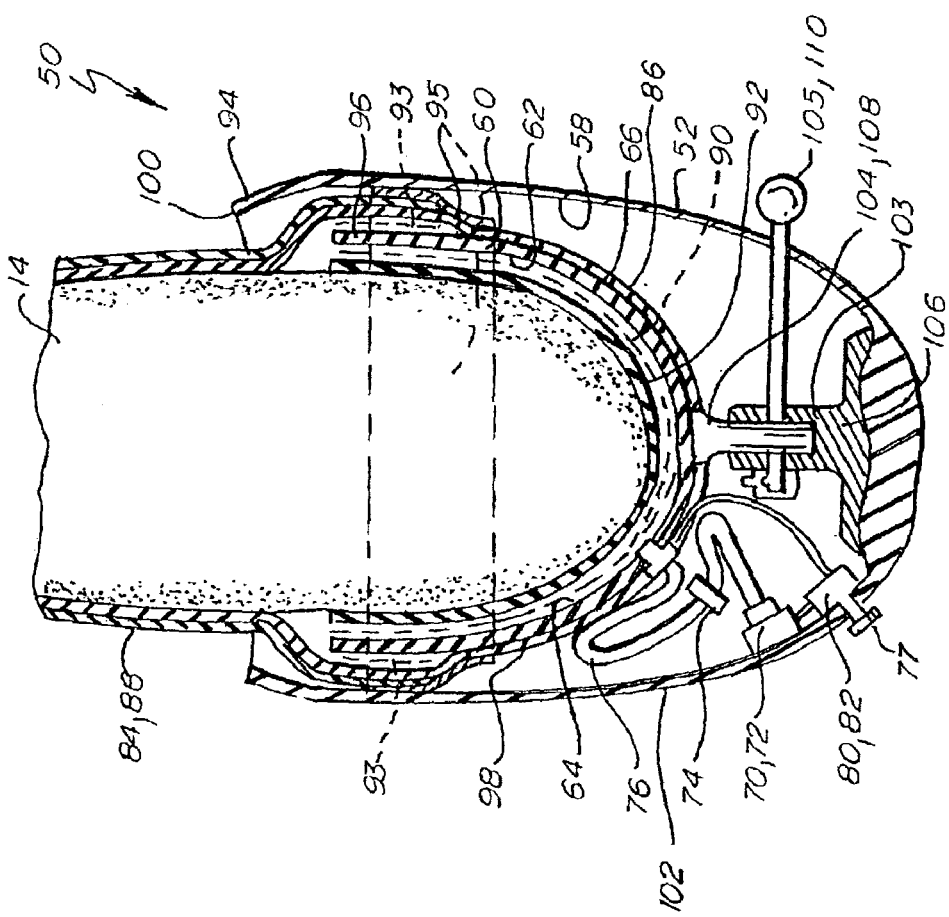
FIG. 13 is a cross-section of the artificial limb showing a seventh embodiment of the artificial limb.

A seventh embodiment of the artificial limb of the present invention is shown in FIG. 13. The seventh embodiment is a variation on the sixth embodiment.

Figure 14:
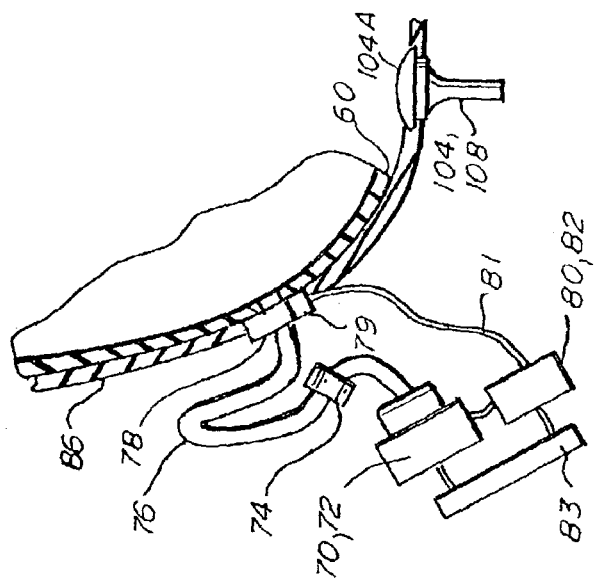
FIG. 14 is a detailed view of the vacuum mechanism and suspension sleeve of FIG. 13.

First, the mechanical interlock 103 does not engage the inner socket 60. Instead, the mechanical interlock engages the outer socket 52 and the suspension sleeve 86. To accomplish this, the suspension sleeve 86 covers the entire inner socket 60, and the suspension sleeve 86 has the extension 104 or shuttle pin 108 embedded in the suspension sleeve at the distal end of the suspension sleeve, as shown in FIG. 14. Preferably, the extension 104 has a portion 104A embedded in the suspension sleeve. This portion 104A may be a disk or umbrella 104A. The extension 104 then engages the docking device 106 as previously described.

Second, the suspension sleeve 86 is modified to support the additional weight imposed on the suspension sleeve 86 due to the outer socket 52 and artificial limb. In particular, the suspension sleeve 86 is fabricated from a material which allows circumferential expansion but resists longitudinal stretching under the weight of the artificial limb. Such a material is described in U.S. Pat. No. 5,571,208, herein incorporated by reference.

The sleeve 86 preferably contains fabric threads which may be oriented circumferentially around the sleeve. The threads preferably are comprised of double-knit polyurethane. The threads may also include nylon. The threads permit the sleeve 86 to expand circumferentially so that the sleeve may be slipped onto the residual limb 14 and so that the lower portion may be slipped over the inner socket 52. The threads are preferably connected together with cross-links, which also may be preferably comprised of polyurethane. The cross-links and threads form a matrix which allows circumferential expansion but resists longitudinal stretching under the weight of the artificial limb. By example, the sleeve 86 may have at or about a 4-to-1 ratio of circumferential stretch relative to longitudinal stretch.

The sleeve 86 may have a portion above the inner socket 52 which is manufactured of material which allows both vertical and horizontal stretching, to increase flexibility.

Figure 15:
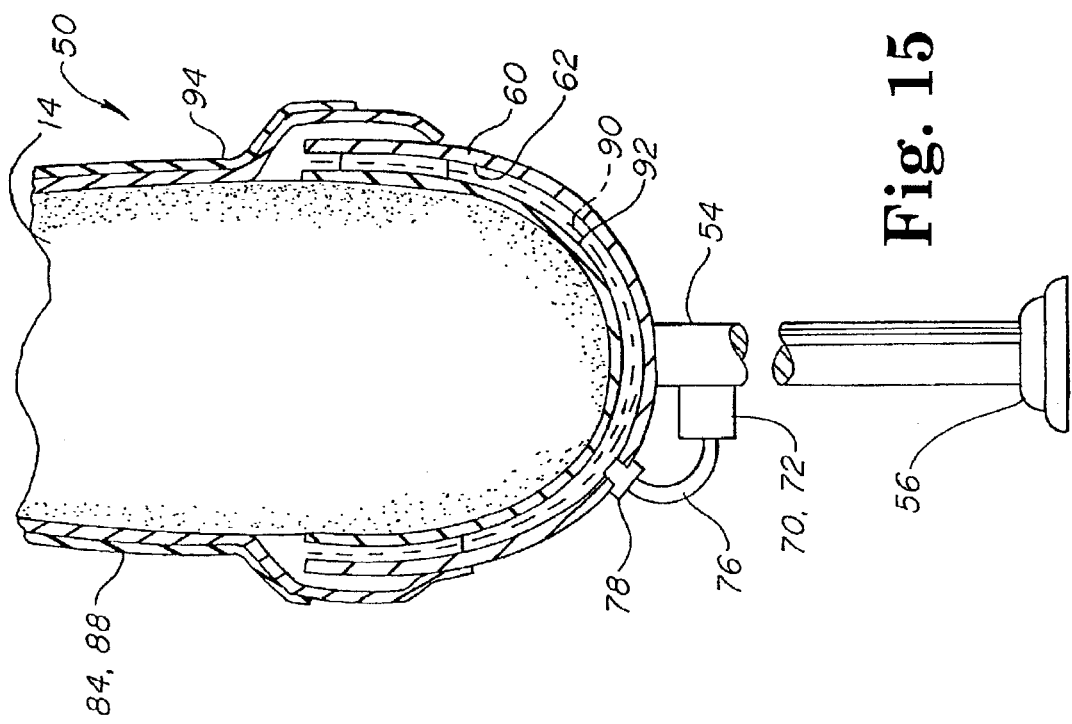
FIG. 15 is a cross-section of the artificial limb showing an eighth embodiment of the artificial limb.

An eighth embodiment of the artificial limb of the present invention is shown in FIG. 15.

Unlike earlier embodiments, the artificial limb 50 of the eighth embodiment has only a single socket 60 rather than inner and outer sockets and is thus considerably simpler.

The socket 60 has a volume and shape to receive a substantial portion of the residual limb 14 with a cavity 62 therebetween.

A nonfoamed, nonporous polyurethane liner 92 is preferably adapted to receive the residual limb 14 and to be disposed between the residual limb 14 and the socket 60.

A vacuum source 70 is connected to the cavity 62 by a vacuum valve 78, thereby drawing the residual limb 14 into firm contact with the socket 60.

A seal means 84 makes a seal between the residual limb 14 and the socket 60 to minimize air leakage into the cavity 62. It has been found that it is difficult to make a perfect seal, with the result that air leakage can occur at rates up to 30 cc per minute. As air leaks into the cavity 62, it is desirable to activate the vacuum source 70 to restore vacuum in the cavity. Furthermore, it has been found that when the vacuum in the cavity is about 5 inches of mercury, the residual limb may lose up to about 6 to about 15% of its volume during the day, whereas if the vacuum in the cavity is at or about 10-25 inches of mercury, the residual limb loses only about 1% of its volume during the day.

Figure 16:
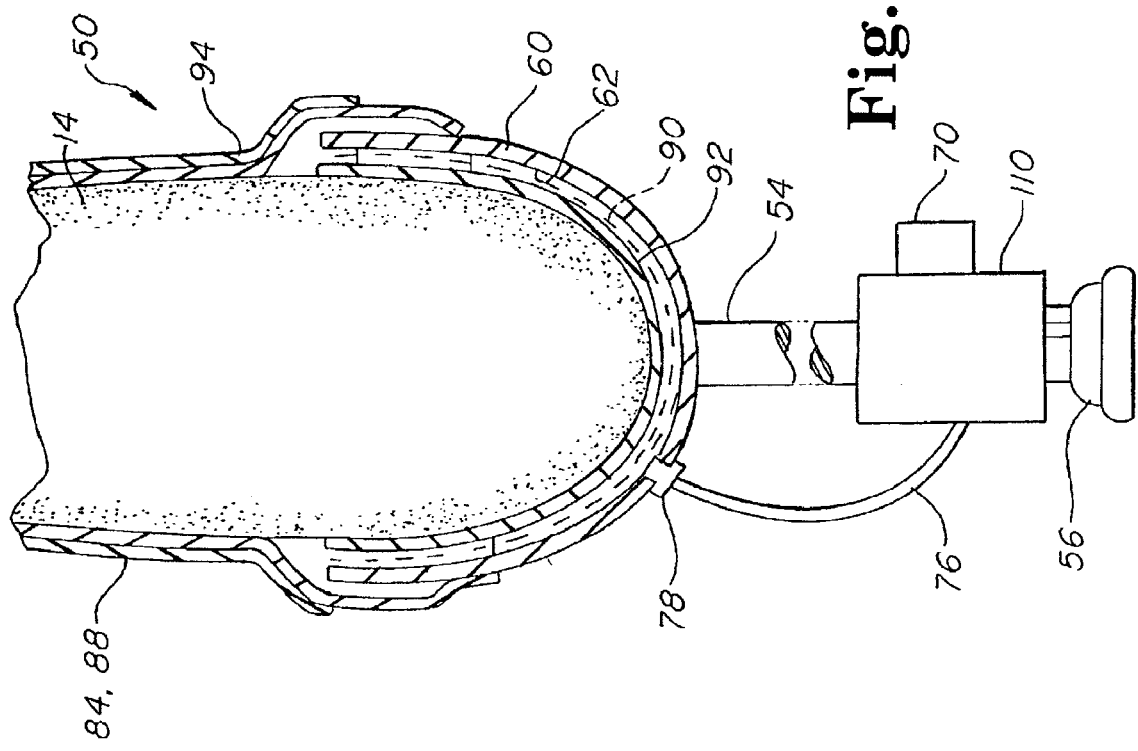
FIG. 16 is a cross-section of the artificial limb showing a ninth embodiment of the artificial limb.

To minimize the time that the vacuum source, such as a vacuum pump 72, needs to run to maintain vacuum in the cavity, a ninth embodiment of the artificial limb 50 is shown in FIG. 16. The ninth embodiment is the same as the eighth embodiment, but a vacuum reservoir 110 is added between the vacuum source 70 and the vacuum valve 78. The vacuum reservoir 110 has a volume substantially larger than the cavity 62. Suitably, the vacuum reservoir may have a volume of about 2 gallons or about 9000 cc while the volume of the cavity 62 is preferably about 100 cc or even less.

It will be seen that as air leaks into the cavity 62, the air will be pulled into the vacuum reservoir 110, thereby maintaining the vacuum in the cavity 62.

When the vacuum in the reservoir 110 reaches a certain minimum threshold, the vacuum source 70 may be activated to restore vacuum to the vacuum reservoir 110. The vacuum source 70 may be activated either manually or by a regulator (not shown).

The artificial limb 50 typically includes a shin or pylon 54 and a foot 56, as shown in FIG. 3. Preferably, the vacuum reservoir 110 is attached to the shin 54 between the socket 60 and the foot 56. However, the vacuum reservoir may also be carried separately, as for example in a backpack. Depending on the placement of the vacuum reservoir 110, a vacuum tube 76 may be necessary to connect the vacuum reservoir 110 to the vacuum valve 78.

If the volume of the vacuum reservoir 110 is at or about 9000 cc and air leaks into the cavity 62 at or about 75 cc per minute, it will be seen that the intervals between activation of the vacuum source 70 can be up to about 120 minutes.

The artificial limb 50 of the eighth and ninth embodiments may preferably further comprise the following.

An inner sheath 90 may be adapted to be disposed between the liner 92 and the socket, to ensure even distribution of vacuum in the cavity 62, as earlier described. Preferably, the inner sheath 90 may be thin knitted nylon. The sheath 90 may also be affixed to the outside of the liner 92.

The seal means 84 is preferably a nonfoamed, nonporous polyurethane suspension sleeve 86 for rolling over and covering the socket 60 and a portion of the artificial limb 14, as earlier described.

A stretchable nylon second sleeve 94 for rolling over and covering the suspension sleeve 86 may be added to prevent clothing from sticking to and catching on the suspension sleeve 86, as earlier described.

The vacuum source 70 is preferably a motor or mechanical driven vacuum pump 72, as earlier described. A vacuum tube 76 may be necessary to connect the vacuum pump 72 to the vacuum valve 78, depending on the placement of the vacuum pump 72.

The vacuum source 70 may also be a weight-actuated vacuum pump and shock absorber, as disclosed in U.S. Pat. No. 6,554,868 and herein incorporated by reference.

To maintain the vacuum in the cavity, either a regulator means 80, a vacuum reservoir 110, or a weight-actuated vacuum pump and shock absorber, as disclosed in U.S. Pat. No. 6,554,868, may be employed.

Applicant has found that one or more of the embodiments discussed earlier share a common problem. The vacuum which holds the residual limb (and liner) in firm contact with the socket tends to cause edema and blistering at the point on the residual limb where the suspension sleeve contacts the residual limb. This problem occurs because the vacuum (perhaps about 7½ pounds of negative pressure) in cavity 62 draws against the suspension sleeve 86 at the point where the suspension sleeve 86 contacts the skin of the residual limb. However, because the liner 92 often has an outer fabric cover 130 to prevent the liner from adhering to the socket 60 or clothing, the suspension sleeve cannot make a good seal at the point where it contacts the outer fabric cover 120. This has left the residual limb as the only point at which to make the seal.

Figures 17, 18:
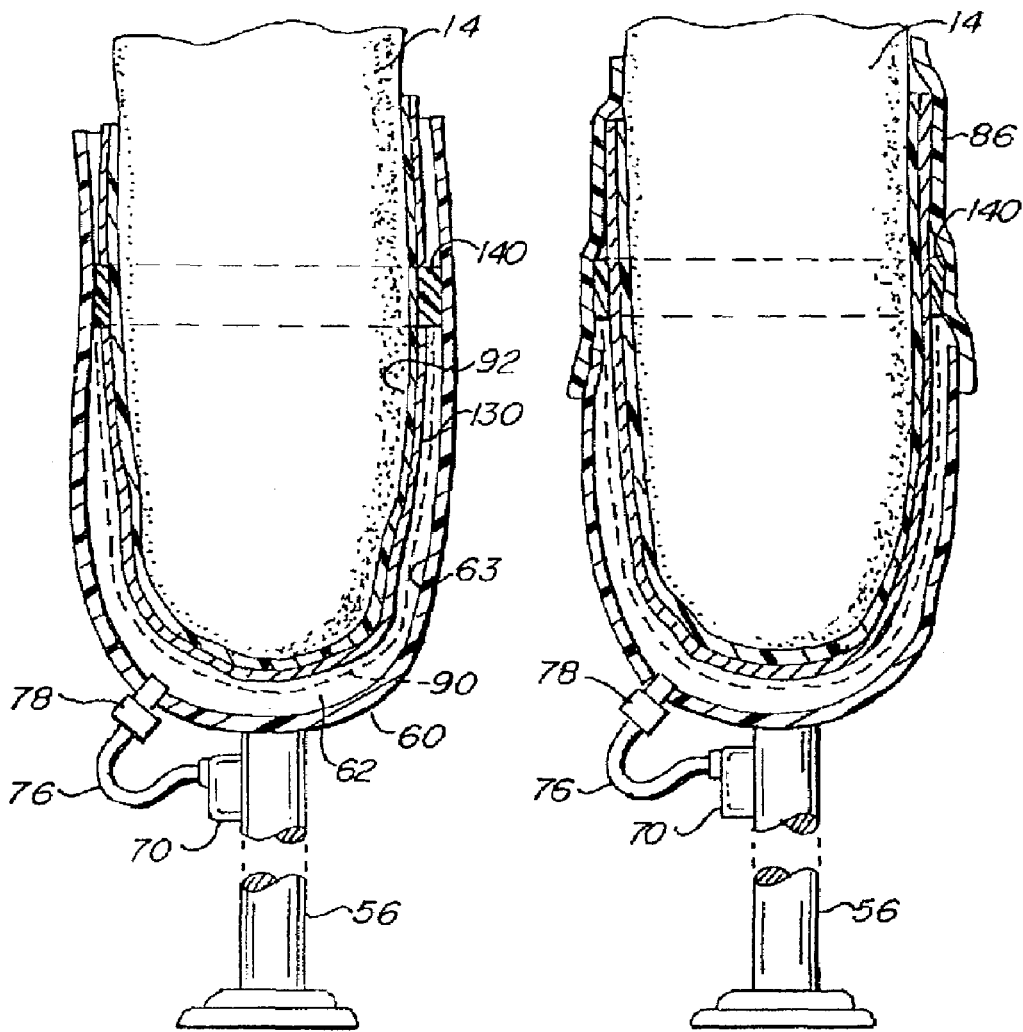
FIG. 17 is a cross section of the artificial limb showing a liner with an annular seal.
FIG. 18 is a cross-section of the artificial limb showing a second embodiment of the liner of FIG. 17.

FIG. 17 shows one solution to this problem. The liner 92 is improved by adding an annular seal 140 extending outwardly from the fabric cover 130. The annular seal, which may be made from the same material as the inner layer 92 of the liner, is adapted to sealingly engage the suspension sleeve 86, producing a seal against the vacuum in cavity 62 at the point of contact with the suspension sleeve 86. Therefore, the vacuum in cavity 62 now draws against the annular seal 130 rather than against the skin of the residual limb 14.

An alternative solution to the above problem is shown in FIG. 18. Here, the annular seal 140 does not make contact with the suspension sleeve 86, but rather makes contact with the inner wall 63 of the socket 60, and makes a seal at that point. No suspension sleeve is used in this variation, it being found that sufficient holding force is provided by the vacuum in cavity 62.

Figure 19:
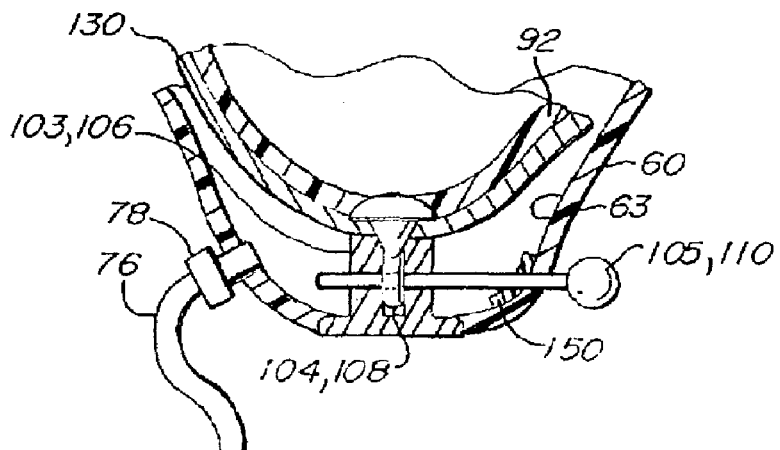
FIG. 19 is a partial cross-section of the artificial limb showing a third embodiment of the liner of FIG. 17.

A second alternative is shown in FIG. 19. This alternative is like that of FIG. 18, with the exception that a mechanical interlock 103 is provided which is adapted to interlock with the socket 60. Preferably, as shown, the mechanical interlock 103 comprises a shuttle pin 108 adapted to connect the liner 92 with the socket 60, and a locking mechanism 105 such as a second pin 110 extending through the socket 60 to the exterior of the socket 60 for access by the amputee as earlier described. More particularly, the liner 92 may have an extension 104 or shuttle pin 108 embedded in the liner at the distal end of the liner. Preferably, the extension 104 has a portion 104A which may be a disk or umbrella which engages a docking device 106 as earlier described.

To reduce the flow of air into the cavity 62, the invention of FIG. 19 also preferably includes a locking mechanism seal 150 adapted to engage the inner wall 63 of the socket 60 about the locking mechanism 105. The seal 150 could alternatively be on the outer surface of the socket 60.

Figure 20:
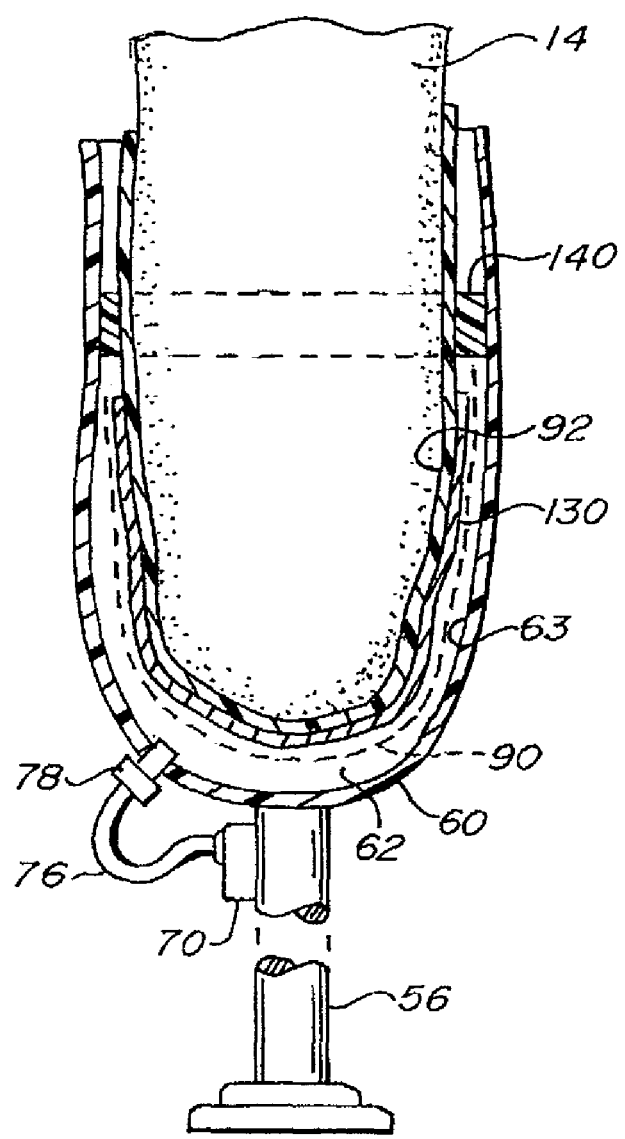
FIG. 20 is a partial cross-section of the artificial limb showing a fourth embodiment of the liner of FIG. 17.

Another alternative is shown in FIG. 20. Here, the fabric cover 130 stops below the annular seal 140. The annular seal 140 may also be made of the same material as the liner 92.

A very important advantage, in all of the above embodiments, is the use of vacuum within the socket to prevent fluids from migrating out of the distal end of the residual limb due to weight-bearing pressures, or at least to reduce this migration.

Application of a vacuum to the socket cavity 62 can suck the liner 92 against the inner wall of the socket 60. The liner 92 can be relatively snug against the residual limb 14 so that the residual limb 14 can be butted up against the inner wall of the inner socket 60. During the weight-bearing phase of walking, the wearer's body weight can force the residual limb 14 and liner 92 more tightly against the inner wall of the socket. However, during the non-weight-bearing phase, or swing phase, of walking, the weight of the artificial limb 50 will have a tendency to cause the inner socket 60 to pull away from the liner 92. This is prevented or reduced by the vacuum in the socket cavity 62. Because the vacuum keeps the liner 92 tightly opposed to the inner wall of the inner socket 60, this tendency will also cause the liner 92 to pull away from the residual limb 14, creating a small, partial vacuum between the liner 92 and the residual limb 14. This small, partial vacuum, perhaps on the order of about 2 inches of mercury, will then oppose the migration of fluids out of the residual limb 14.

In order for this beneficial effect of vacuum to occur, the vacuum in the socket cavity 62 is preferably at least about 10 to 25 inches of mercury. At this level of vacuum, it has been found with some wearers that the residual limb loses only about 1% of its volume during the day.

Figure 21:
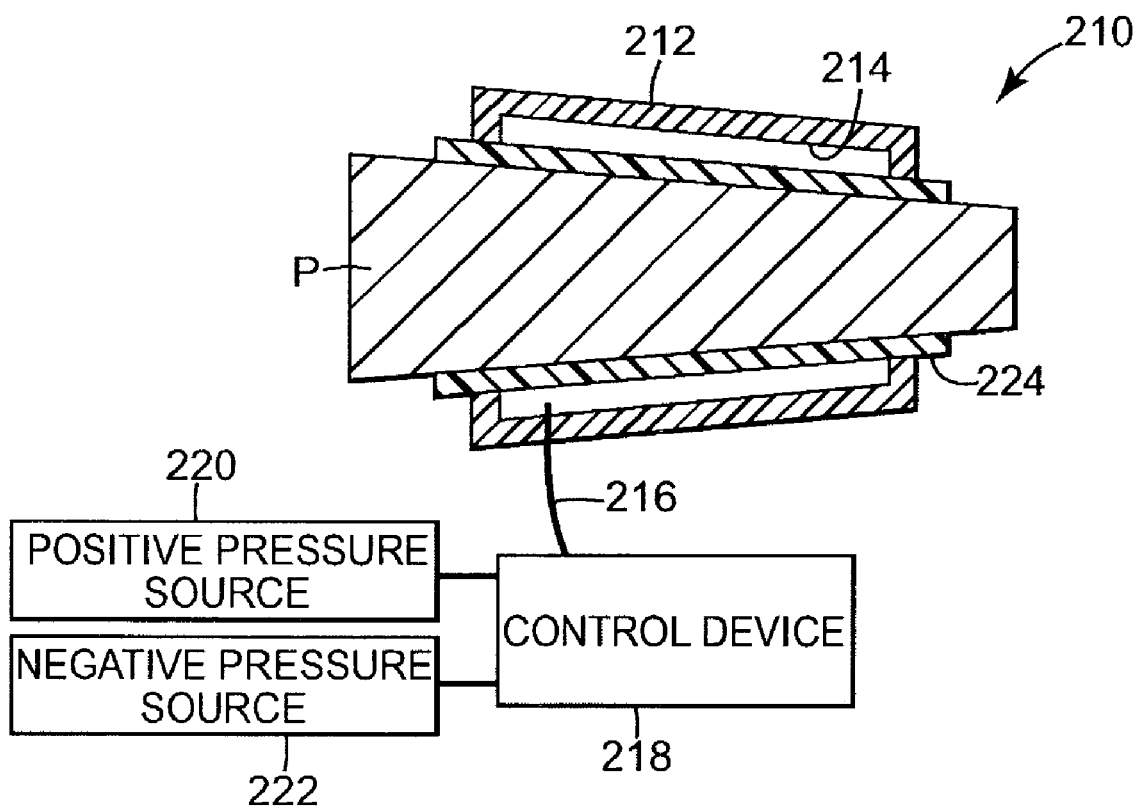
FIG. 21 is a schematic of one embodiment of a pressure chamber apparatus with a body part inserted.

Referring now to FIG. 21, a schematic of a first embodiment of a pressure therapy apparatus 210 of the present invention is shown. The apparatus 210 preferably comprises a sealed chamber 212 having an interior 214 with a pressure line 216 entering the interior 214. The pressure line 216 is connected to a control device 218. The control device 218 is, in turn, connected to a positive pressure source 220 and a negative pressure source 222. Although shown as separate positive and negative pressure sources, 220, 222, it is to be understood that a single pressure source capable of providing both positive and negative pressures may also be used.

In this first embodiment, a body part "P" is enclosed in a liner 224, and the body part P and liner 224 are inserted into the chamber 212. The liner 224 is preferably constructed of a flexible urethane, although other materials may also be used. The chamber 212 can be configured to generally conform to the shape of the body part P (such as a trunk, hand, arm, foot, leg, portions thereof or the residuum thereof following a partial amputation thereof), as shown in FIG. 21. That is, the chamber 212 can be anatomically shaped to conform to and surround the portion of the body part to which pressure therapy is to be applied. This configuration reduces the overall volume of the chamber as compared to prior pressure chambers usually formed as large boxes into which a body part is placed. Reduced volume of the chamber 212 results in enhanced control over the fluid volume in the body part P, thereby reducing the occurrence or degree of edema, the accumulation of fluid in a body part. Better control over fluid volume provides more variability in the time and amount of pressure therapy that may be applied to the body part, without causing or at least reducing negative side effects. That is, a smaller volume chamber, such as chamber 212, can allow for longer pressure therapy sessions or overall duration without causing or at least reducing significant edema or other problems for the patient. The chamber 212 can be said to provide a means for applying pressure to the portion of the body or body part P.

The liner 224 can extend over the body part P and beyond the boundaries of the chamber 212, such that the chamber 212 can seal to the liner 224 and not to the body part P directly, as shown in FIG. 21. As a result, the positive and negative pressure can be applied to the liner 224 and not the skin of the patient. Use of the liner 224, such as a urethane liner, allows for equalization of the pressure being applied (both positive and negative). Certain urethane liners are known to be semi-fluid and allow for the distribution or re-distribution of force over the surface area of the urethane liner. As a result, the body part P is subjected to less trauma and thus more beneficial pressure therapy may be provided. The liner 224 can be said to provide a means for sealing and/or a means for equalizing, distributing, or redistributing pressure.

Figure 22:
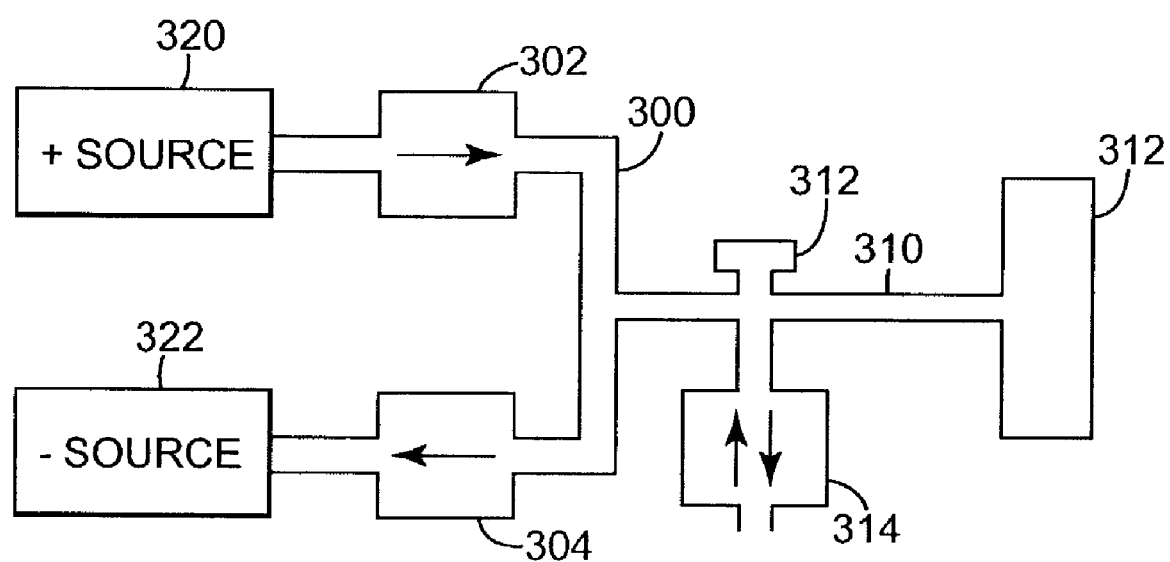
FIG. 22 is a detailed pneumatic schematic of one embodiment of the apparatus and control mechanism.

Pressure in the chamber 212 can then be controlled by a circuit, such as, for example, the device 218. The device 218 can control the amplitude of the positive and negative pressure and/or the frequency at which the positive and negative pressure can be oscillated. One embodiment of a representative pneumatic schematic diagram is shown in FIG. 22. In this embodiment, a pneumatic connection 300 can be coupled to a positive pressure source 320 and is controlled by a normally closed electronic solenoid 302. The pneumatic connection 300 can also be coupled to a negative pressure source 322 and is controlled by a normally closed electronic solenoid 304. The pneumatic connection 300 can be coupled to a chamber 312 via a second connection 310, in which an absolute pressure sensor 312 and a bleed to atmosphere 314 can be fluidly coupled. The absolute pressure sensor 312 can be configured to sense both positive and negative pressures. The bleed to atmosphere 314, as shown, can also be a normally closed electronic solenoid. Computer or other programmable control of the solenoids 302, 304, 314 and sensor 312 provide the desired pressure cycles within the chamber 312, as well as better optimization, increased control of the pressure chamber and pressure therapy, and feedback capability. All or portions of the components noted in this paragraph can be referred to as means for controlling pressure.

Figure 23:
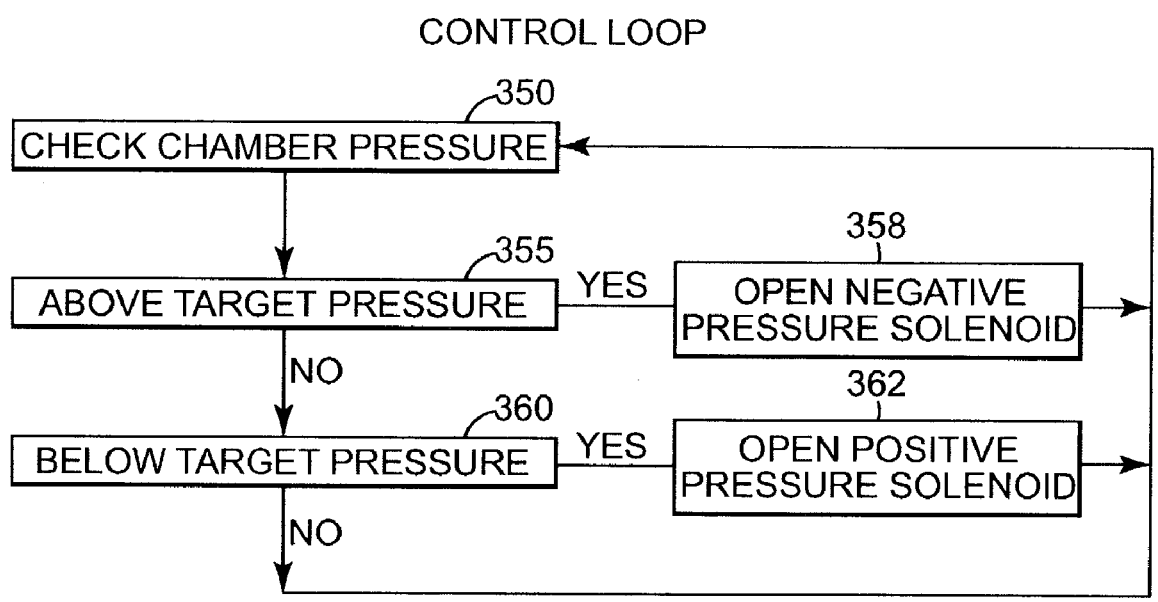
FIG. 23 is a flowchart of a control loop for an embodiment of the present invention.

One embodiment of a representative pressure control flow chart is shown in FIG. 23. In this embodiment, the pressure of the chamber 312 (FIG. 22) can be checked in step 350. The pressure can then be compared to a desired targeted value and evaluated as to whether the sensed pressure is above the targeted value, in step 355. If above a negative pressure solenoid 304 (FIG. 21) can be opened, in step 358. The pressure can then be checked again in step 350. If not above, the sensed pressure can be evaluated as to whether it is below the targeted value, in step 360. If below, the positive pressure solenoid 302 can be opened, in step 362. The pressure can then be checked again in step 350. If not below, the pressure can be checked again in step 350. This loop can be repeated as needed during the pressure therapy session.

Preferably, the positive and negative pressure is applied to the body part P in a wave cycle (preferably a sine wave). This wave could be altered or possibly synchronized to the rhythm of the heart to assist in blood flow. In one embodiment, the control device 218 can be coupled to a heart rate monitor or other sensor allowing for feedback to the control device 218 (FIG. 21) in order to synchronize the pressure wave cycle to the rhythm of the heart of the patient or the blood flow in the particular body part being treated.

As the positive pressure is applied, a volume of blood can be evacuated from the body part P in the area inside the chamber. When the negative pressure is applied, a volume of blood is pulled into the body part P in the area in the chamber. Since blood can flow only in one direction in a blood vessel of the human body, this is intended to provide a fresh supply of blood to the body part P in the area inside the chamber.

In a second embodiment, the apparatus may comprise a bandage or patch that makes a sealed contact with an area of the skin, rather than a chamber into which a body part is inserted. As with the first embodiment, a liner portion is provided as part of the bandage or patch over the skin with the pressure portion applied to the liner portion, instead of directly to the skin. The bandage or patch can be attachable by an adhesive or by another fastening mechanism.

Figure 24:
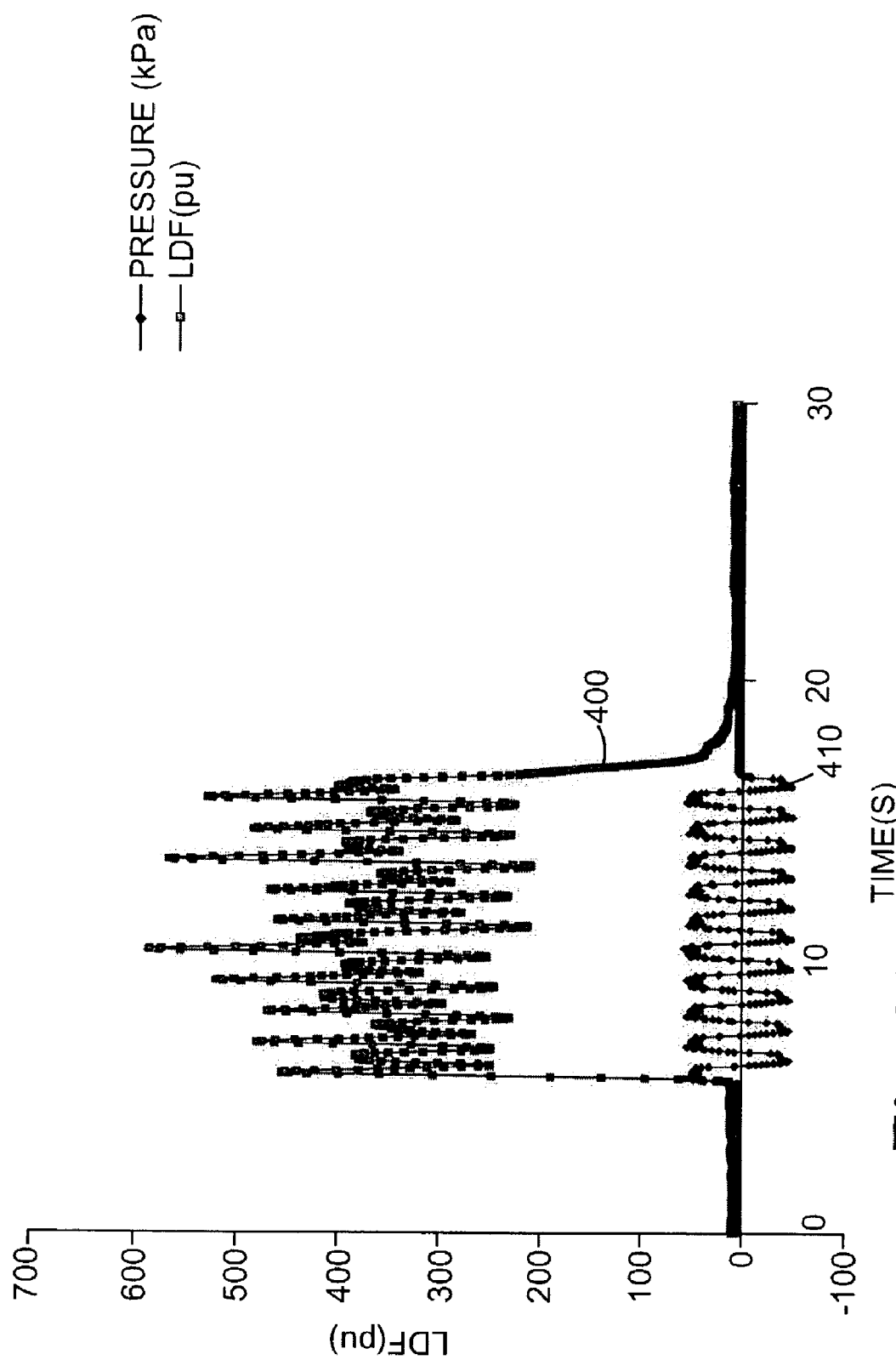
FIGS. 24 and 25 are charts showing the variation of blood flow to a body part compared to the pressure cycle produced by the apparatus.
Figure 25:
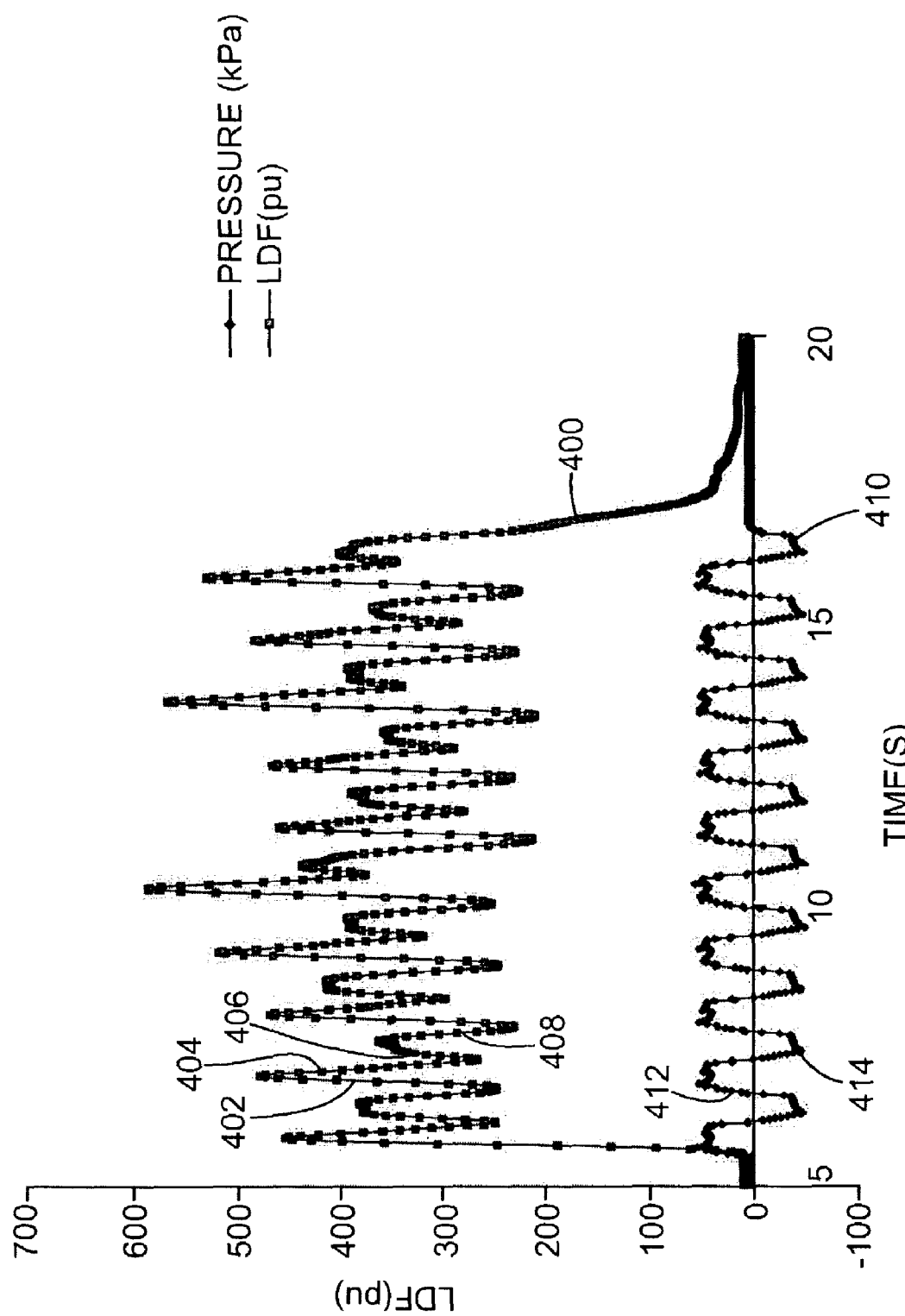

FIGS. 24 and 25 show the relationship between measured blood flow 400 in the body part and the pressure cycle 410 applied to the body part. As can be seen in the graphs, and most clearly in FIG. 25, as a positive pressure 412 can be applied, blood flow increases 402 until the positive pressure constricts the vessels or significantly reduces the fluid volume in the body, thus causing blood flow to drop 404. The subsequent application of a negative pressure 414 results in another increase in blood flow 406, but only to a limit at which time the blood flow again drops off 408. This cycle is repeated as the positive and negative pressures are repeated. Overall, however, blood flow is generally increased during the pressure therapy. Most preferably, the range of pressures that the apparatus may employ is from at or about 30 to at or about 760 mm. Hg (at or about 0.6 to at or about 15 psi) positive pressure and from at or about −30 to at or about −640 mm. Hg. (at or about −0.6 to at or about −12 psi) negative pressure. Cycle frequency may vary, but it can be at or about 1 second/per cycle, as shown in FIGS. 24 and 25 or it can be optimized according to avoid reaching or closely approaching constrictive limits causes by a duration of positive or negative pressure.

The present invention provides an artificial limb for an amputee, which includes a socket configured to provide pressure therapy to the residual limb within the socket in order to manage fluid within the residual limb, enhance blood flow, improve wound healing and/or to maintain or improve the condition of the residual limb. The residual limb of the amputee may also be known as the residuum. In the socket embodiments described previously, numerous configurations were provided to achieve a total or nearly total contact connection or relationship with the residual limb. As a result, as a wearer walks, the residual limb experiences changes in pressure due to the artificial limb, including the socket, being worn by the wearer. When a step is taken, the weight applied to the artificial limb results in increased positive pressure on the residual limb within the socket. As discussed previously, this positive pressure pushes fluid out of the vessels and tissue of the residual limb.

When the weight is removed, during a swing phase of the walking stride when the weight is on the other leg, the artificial limb in essence tries to remove itself from the residual limb due to momentum and centrifugal force, but such movement is resisted by the seal created at the socket. It has been found that with artificial limbs and sockets described above, the total or nearly total contact provided with the residual limb results in a physical link between the socket and the limb tissue through the liner. During this swing phase, as the socket tries to move away from the residual limb, the limb tissue tries to pull away from the limb bone. Because connective tissue connects the limb tissue to the bone, this pulling away of the limb tissue is resisted, but potential minor displacement between the limb tissue and bone occurs. As a result, a negative pressure hypodermic effect is created within the tissue, which can cause fluid, including blood, to be pulled into vessels in the tissue.

Figure 26:
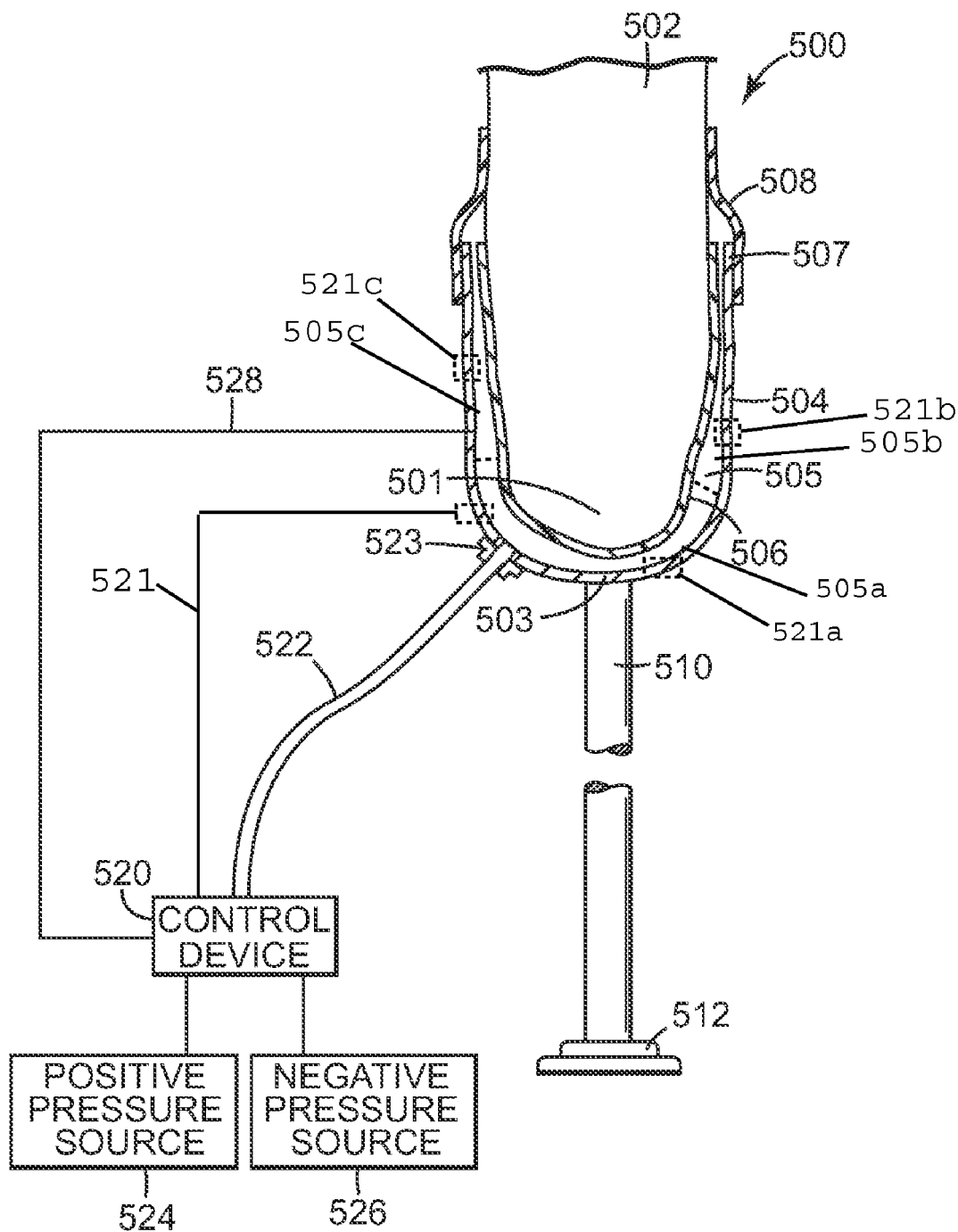
FIG. 26 is a cross-section of another embodiment of an artificial limb including a pulsating pressure chamber.

Walking by an amputee wearing such an artificial limb thus results in some degree of alternating positive and negative pressure being applied to the tissue of the residual limb. Referring now to FIG. 26, a simplified schematic of a first embodiment of a therapeutic artificial limb for amputees is shown. In this embodiment, a residual limb 502 of a wearer is received within a socket 504. The residual limb 502 is covered by a liner 506. A chamber 505 is formed between the residual limb 502 and the socket 504. An over sleeve 508 may be worn to cover the residual limb 502 and socket 504, along with other inner sleeves and stockings, as described above but not shown for clarity. The socket 504 is coupled to a pylon 510, or other structural member forming the artificial limb 500, as needed, and a foot 512. The artificial limb 500 may include a knee joint, an elbow joint, a hand, or connections thereto, or any other appropriate components based on the extremity that was amputated and the needs of the wearer. The components coupled to the socket 504 may also be known as a prosthesis, a prosthetic device or a prosthetic limb. Details of the various connections possible between the prosthesis and socket 504 are described above or in other appropriate literature.

A control device 520, including but not limited to a programmable controller, microprocessor and/or a computer, connects to the chamber 505 within the socket 504 via a supply line 522. The control device 520 also connects to either a positive pressure source 524, a negative pressure source 526, or both, depending on the desired output of the therapeutic artificial limb 500. Alternatively, the control device 520 may be connected to a single pressure source configured to provide both negative and positive pressures. The connection 522 to the socket 504 may include a fitting 523 configured to appropriately connect and seal the connection 522. The fitting 523 may include a quick release coupling, a mechanical fastener, an adhesive, a valve, or other necessary device usable for a pressure line connection. Although shown with a single connection 522, it is to be understood that multiple connections may also be used, as needed or desired. These multiple connections may be distributed about the socket 504 with respect to the residual limb 502 and may be provided in predetermined multiple zones or sections from a bottom end 503 toward a top end 507 or circumferentially around the socket 504, or both bottom-to-top and circumferential. Optionally, one or more of the connections from the control device 520 may be provided to the liner 506 so as to provide pressure to liner 506; preferably, however, at least one connection is provided to the socket chamber 505.

The control device 520 and pressure source or sources 524, 526 may be provided in conjunction with the pylon 510, such as mounted to the pylon 510 or formed as part of the pylon 510. Alternatively, these components may be provided on or with the socket 504. Optionally, these components may be provided separately from both the socket 504 or the pylon 510, and may be worn in a belt or other harness by the wearer. Other mounting and/or harnessing options are also possible.

The socket 504 is configured to conform in volume and shape to the residual limb 502 of the wearer. The liner 506 covers the limb 502 and seals to the socket 504. The liner 506 is preferably formed from a flexible material, including urethane, polyurethane or other appropriate materials. Various embodiments of the liner 506 are described in more detail above. Optionally, the liner 506 may be provided with ribs or ridges that may interact with the socket 504 so as to provide multiple zones or sections within the chamber 505 (or multiple mini-chambers) for added pressure control about the residual limb 502, i.e., pressure can be different and controlled in the multiple zones or regions.

The embodiment shown in FIG. 26 of a therapeutic artificial limb 500 can provide all of the same functional capabilities as the socket and artificial limb embodiments described above. The control device 520 controls the application of negative pressure or vacuum to the socket 504, so as to achieve similar benefits, including securement of the prosthesis and socket 504, proper fit, adaptation for residual limb volume changes due to fluid loss or swelling, and retention of the artificial limb on the residual limb through negative pressure, to name a few. In addition, this embodiment provides for the alternating positive and negative pressures required to achieve the desired therapeutic effect on the residual limb.

Although walking or running by the wearer can result in some therapeutic effect, these effects are appropriately controlled and are more controllable through the control device 520. Should more or less positive or negative pressure be required during walking, running or resting, the control device 520 provides the appropriate pressures from the positive and negative pressure sources 524, 526.

When a wearer is at rest, that is, the wearer is not walking but still is wearing the therapeutic artificial limb 500, or when the therapeutic artificial limb 500 is provided on an upper extremity, the control device 520 provides the alternating positive and negative pressures required to achieve the desired pressure therapy for the residual limb 502. When, where and how the pressure therapy is applied to the residual limb 502 is a variable controlled by the control device 520. For example, therapy may be applied only during walking, it may be applied only during resting, or it may be applied during both walking and resting. A doctor or therapist may prescribe the required amount and manner of the pressure therapy for a wearer, programming the control device 520 accordingly. A wearer may have manual control over the therapy or may have access to switch between different settings and options on the therapeutic artificial limb 500, such as by switching between negative and positive pressure, adjusting the amplitude and/or frequency of the oscillations or otherwise controlling the therapy. Alternatively or in addition, the control device 520 may vary the amount and manner of therapy needed based on sensor input from the socket 504 or residual limb 502.

The control device 520 may also be provided with sensory feedback from the socket 504 or residual limb 502, such as through a sensor connection 528. Sensors that may be used with the therapeutic artificial limb 500 include, but are not limited to, blood flow, temperature and/or fluid volume in the residual limb, heart rate of the wearer, and/or environmental variation in the socket 504 or other portion of the artificial limb 500. These sensors may be provided for general feedback within the socket 504 or residual limb 502, and may be mounted or otherwise provided on the socket 504, within the chamber 505, in the liner 506 or on the residual limb 502.

Alternatively, the sensors maybe provided as multiple sensors configured in zones or regions around the socket 504 or limb 502, separate from or in conjunction with the multiple pressure inputs and zones or regions described above. These multiple sensors may then be monitored in zones or in localized areas of the socket 504 or limb 502. As a result, specialized therapy for specific areas of the residual limb 502 may be provided to address particular concerns, such as a wound, a bony protrusion or prominence, an area of decreased vascular flow or swelling, or other potential problems that the wearer may have. Therapy may be removed from or lessened within a zone or area, it may be increased within a zone or area, or it may be applied only to a specific zone or area. For example, a gradient pressure may be provided with increased pressure at distal end 501 of the limb 502 and decreasing pressure moving away from the distal end 501.

Optionally, a pressure patch, such as those described above, including one or more dedicated pressure inputs from the control device 520, may be provided on the limb 502. These pressure patches may be placed on top of or underneath the liner 506, so as to provide targeted pressure therapy to a specific location on the residual limb 502 to address specific problems without the need to use a socket 504 having multiple sensors and/or multiple pressure inputs.

The therapeutic artificial limb 500 of the present invention also provides a mechanism whereby medicines and/or drugs may be delivered to an area of a residual limb 502, in an efficient manner. The pressure therapy as described, that is the alternating positive and negative pressures, pulls the blood into the residual limb 502, which in turn can deliver the desired drugs through the blood stream. Use of the zone therapy would allow for focused drug delivery to a particular wound, chronic sore or other area in need of medicinal treatment.

The present invention may be embodied in other specific forms without departing from the spirit or essential attributes thereof, and it is therefore desired that the present embodiment be considered in all respects as illustrative and not restrictive. Along these lines, variations and different combinations of the features, components and method steps mentioned herein are contemplated. Also, as noted previously, one or more of the features, components or method steps can be eliminated or replaced by something that provides the same or similar intended effect.

What is claimed is:

1. An apparatus for securing a prosthesis to the residuum of a limb of an amputee and for providing pressure therapy to the residuum, the apparatus comprising:
    a socket shaped to receive a residuum of a limb of an amputee and configured to also be connected to a prosthetic limb, wherein the socket is also shaped to form a chamber between an inner surface of the socket and the residuum when the residuum has been received within the socket; and
    a pressure control device operably connected to the chamber, which creates positive pressure and negative pressure within the chamber for providing pressure therapy to the residuum received within the socket, wherein the pressure control device is programmed to oscillate the positive and negative pressures at a predetermined amplitude and frequency.

2. The apparatus of claim 1, wherein the pressure control device is configured to affect securement of the socket to the residuum.

3. The apparatus of claim 1, further comprising a liner adapted to surround at least a portion of the residuum and function as a seal between the socket and the residuum.

4. The apparatus of claim 3, wherein the liner is adapted to surround substantially the entire residuum.

5. The apparatus of claim 3, wherein the liner comprises urethane.

6. The apparatus of claim 1, wherein the pressure control device is configured to change the pressure within the chamber in connection with a change between the weight-bearing phase of the amputee's stride and the swing phase of the amputee's stride.

7. The apparatus of claim 6, wherein the pressure control device is configured to create positive pressure during the swing phase and negative pressure during the weight-bearing phase.

8. The apparatus of claim 6, wherein the pressure control device is configured to create negative pressure during the swing phase and positive pressure during the foot strike phase.

9. The apparatus of claim 1, wherein the pressure control device is configured to enable the amputee to adjust the amplitude of the pressure within the chamber.

10. The apparatus of claim 1, wherein the pressure control device is configured to enable the amputee to control whether the chamber is under positive pressure or negative pressure.

11. The apparatus of claim 1, wherein the pressure control device is configured to adjust the pressure in the chamber based on whether the amputee is standing, walking, or running or is not bearing weight on the prosthesis.

12. The apparatus of claim 11, wherein the residuum contains a fluid volume, and wherein the pressure control device is configured to adjust the pressure in the chamber based on changes to the fluid volume.

13. The apparatus of claim 1, wherein the pressure control device is couplable to a heart rate sensor configured to sense the heart rate of the amputee, and wherein the pressure control device adjusts the pressure in the chamber based on input from the heart rate sensor.

14. The apparatus of claim 1, further comprising a sensor positioned relative to the residuum to sense an attribute useful for at least one of securing the socket to the residuum and providing pressure therapy to the residuum.

15. The apparatus of claim 1, further comprising a plurality of sensors positioned relative to the residuum to sense localized attributes useful for at least one of securing the socket to the residuum and providing pressure therapy to the residuum.

16. The apparatus of claim 15, wherein the operable connection of the pressure control device to the chamber comprises a plurality of pressure inputs distributed relative to the residuum, and wherein the pressure control device provides area specific pressure therapy to the residuum based on sensory input from the plurality of sensors and provided by the plurality of pressure inputs.

17. The apparatus of claim 1, wherein the operable connection of the pressure control device to the chamber comprises a plurality of pressure inputs distributed relative to the residuum.

18. The apparatus of claim 17, wherein at least one of the plurality of pressure inputs connects to a liner adapted to surround at least a portion of the residuum and function as a seal between the socket and the residuum.

19. The apparatus of claim 1, further comprising the prosthetic limb connected to the socket.

20. The apparatus of claim 1, wherein the pressure control device controls the pressure within the chamber based on input by the amputee.

21. An apparatus for securing a prosthesis to the residuum of a limb of an amputee and for providing pressure therapy to the residuum, the apparatus comprising:
   a socket shaped to receive a residuum of a limb of an amputee and configured to also be connected to a prosthetic limb, wherein the socket is also shaped to form a chamber between an inner surface of the socket and the residuum when the residuum has been received within the socket; and
   a pressure control device operably connected to the chamber, which creates positive pressure and negative pressure within the chamber for providing pressure therapy to the residuum received within the socket, wherein the pressure control device is configured to adjust the pressure in the chamber based on input from sensors that sense at least one of location of the residuum, location of a liner on the residuum, temperature of the residuum, temperature of a liner on the residuum, and blood gas within tissue of the residuum.

22. The apparatus of claim 21, wherein the pressure control device is configured to adjust the pressure within the chamber based on input by the amputee.

23. The apparatus of claim 21, wherein the pressure control device is configured to enable the amputee to adjust the amplitude of the pressure within the chamber.

24. The apparatus of claim 21, wherein the pressure control device is configured to adjust the pressure in the chamber based on whether the amputee is standing, walking, or running or is not bearing weight on the prosthesis.

25. The apparatus of claim 21, wherein the pressure control device is couplable to a heart rate sensor configured to sense the heart rate of the amputee, and wherein the pressure control device is configured to adjust the pressure in the chamber based on input from the heart rate sensor.

26. An apparatus for securing a prosthesis to the residuum of a limb of an amputee and for providing pressure therapy to the residuum, comprising:
   means for receiving a residuum of a limb of an amputee and connecting the residuum to a prosthetic limb, wherein the receiving and connecting means forms a chamber between an inner surface of the receiving and connecting means and the residuum when the residuum has been received by the means for receiving; and
   means for controlling fluid pressure within the chamber, which creates positive fluid pressure and negative fluid pressure within the chamber to provide pressure therapy to the residuum received within the means for receiving, wherein the means for controlling pressure is programmed to oscillate the positive and negative pressures at a predetermined amplitude and frequency.

27. The apparatus of claim 26, wherein the means for controlling pressure is capable of affecting securement of the socket to the residuum.

28. The apparatus of claim 26, wherein the means for receiving a residuum comprises a socket shaped to receive the residuum.

29. The apparatus of claim 28, further comprising a liner adapted to surround at least a portion of the residuum and function as a seal between the socket and the residuum.

30. The apparatus of claim 26, wherein the means for controlling pressure is configured to change the pressure within the chamber in connection with a change between the foot strike phase of the amputee's stride and the swing phase of the amputee's stride.

31. The apparatus of claim 26, wherein the residuum contains a fluid volume, and wherein the means for controlling pressure is configured to adjust the pressure in the chamber based on changes to the fluid volume.

32. The apparatus of claim 26, further comprising a sensor positioned relative to the residuum to sense an attribute useful for at least one of securing the means for receiving a residuum to the residuum and providing pressure therapy to the residuum.

33. The apparatus of claim 26, wherein the means for controlling fluid pressure within the chamber is configured to adjust the pressure within the chamber based on input by the amputee.

34. An apparatus for securing a prosthesis to the residuum of a limb of an amputee and for providing pressure therapy to the residuum, comprising:
   means for receiving a residuum of a limb of an amputee and connecting the residuum to a prosthetic limb, wherein the receiving and connecting means forms a chamber between an inner surface of the receiving and connecting means and the residuum when the residuum has been received by the means for receiving; and
   means for controlling fluid pressure within the chamber, which creates positive fluid pressure and negative fluid pressure within the chamber to provide pressure therapy to the residuum received within the means for receiving, wherein the means for controlling pressure is configured to adjust the pressure in the chamber based on input from sensors that sense at least one of location of the residuum, location of a liner on the residuum, temperature of the residuum, temperature of a liner on the residuum, and blood gas within tissue of the residuum.

35. The apparatus of claim 34, wherein the means for controlling fluid pressure within the chamber is configured to enable the amputee to adjust the amplitude of the pressure within the chamber.

36. The apparatus of claim 34, wherein the means for controlling fluid pressure within the chamber is configured to adjust the pressure in the chamber based on whether the amputee is standing, walking, or running or is not bearing weight on the prosthesis.

37. The apparatus of claim 34, wherein the means for controlling fluid pressure within the chamber is couplable to a heart rate sensor configured to sense the heart rate of the amputee, and wherein the means for controlling the fluid pressure within the chamber is configured to adjust the pressure in the chamber based on input from the heart rate sensor.

38. A method for securing a prosthesis to the residuum of a limb of an amputee and for providing pressure therapy to the residuum when the amputee is using a prosthetic limb, the method comprising:
   placing a socket onto a residuum of a lower limb of an amputee, wherein the socket is shaped to receive the residuum and is configured to connect to a prosthetic lower limb, and wherein the socket is also shaped to form a chamber between an inner surface of the socket and the residuum when the residuum has been received within the socket; and
   controlling a change between positive and negative pressure within the chamber to provide pressure therapy to the residuum by oscillating the positive and negative pressures at a predetermined amplitude and frequency.

39. The method of claim 38, wherein the controlling step comprises affecting securement of the socket to the residuum.

40. The method of claim 38, wherein the controlling step comprises changing the pressure within the chamber in connection with a change between the foot strike phase of the amputee's stride and the swing phase of the amputee's stride.

41. The method of claim 38, wherein the controlling step comprises changing the pressure within the chamber based on input by the amputee.

42. The method of claim 38, wherein the controlling step comprises adjusting the pressure within the chamber based on whether the amputee is standing, walking, running or not bearing weight on the prosthesis.

43. The method of claim 38, wherein the controlling step comprises adjusting the pressure within the chamber based on changes in fluid volume within the residuum.

44. The method of claim 38, wherein the controlling step comprises monitoring characteristics of the residuum and adjusting the pressure in the chamber based on the monitored input.

45. The method of claim 38, wherein the controlling step comprises monitoring characteristics of a liner surrounding at least a portion of the residuum and adjusting pressure in the chamber based on the monitored input.

46. The method of claim 38, wherein the controlling step comprises monitoring characteristics of the chamber and adjusting pressure in the chamber based on the monitored input.

47. The method of claim 38, wherein the controlling step comprises monitoring a plurality of sensors positioned relative to the residuum and adjusting pressure about the residuum based on the input from the plurality of sensors.

48. The method of claim 47, wherein the controlling step further comprises adjusting the pressure within the chamber differently in one area of the chamber than another area of the chamber.

49. A prosthesis for a residuum of a leg comprising:
a flexible liner adapted to cover a portion of the residuum;
only a single a socket attached to a prosthetic leg, wherein the socket includes an inner socket surface configured to receive the liner and residuum to form a chamber between and adjacent to the liner and the inner socket surface when the residuum is positioned within the socket, and wherein the socket is configured to allow fluid pressure within the chamber to create a suction force to hold the residuum in the socket;
a vacuum device fluidly connected to the chamber to apply a fluid pressure to the chamber when the residuum is positioned within the socket; and
a pressure control device configured to change an amplitude of the fluid pressure applied by the vacuum pump, wherein the pressure control device is programmed to oscillate between predetermined pressure amplitudes each in the range of between 30 and 760 mmHg.

50. The prosthesis of claim 49, wherein the liner provides a seal between the residuum and the socket.

51. The prosthesis of claim 49, wherein the pressure control device controls at least one of amplitude and frequency of the changes of pressure within the chamber.

52. The prosthesis of claim 49, wherein the pressure control device comprises at least one of a computer, microprocessor, and programmable controller.

53. The prosthesis of claim 49, wherein the predetermined pressure amplitudes comprise a first amplitude less than a pressure outside the socket and a second amplitude greater than the pressure outside the socket.

54. The prosthesis of claim 49, wherein the pressure control device provides pressure therapy to the residuum.

55. The prosthesis of claim 49, wherein the pressure control device is configured to change the pressure within the chamber responsive to at least one of a weight-bearing phase of a stride, a swing phase of the stride, standing, walking, running, and non-weight-bearing.

56. The prosthesis of claim 49, wherein the pressure control device is configured to change the pressure within the chamber responsive to a change in a volume of the residuum.

57. The prosthesis of claim 49, wherein the pressure control device is configured for regulating the pressure within the chamber responsive to input from at least one of a blood flow sensor, blood gas sensor, temperature sensor, pressure sensor, heart rate sensor, residuum volume sensor, and residuum fluid volume sensor.

58. The prosthesis of claim 49, wherein the pressure control device is configured for medicine or drug delivery.

59. The prosthesis of claim 49, wherein the pressure control device is configured for controlling a pressure gradient between zones of the chamber.

60. A method for use with a residuum of leg comprising:
placing the residuum into a flexible liner that covers a portion of the residuum;
placing the residuum and liner only into a single socket to form a chamber between and adjacent to an inner surface of the socket and the liner, wherein the socket is attachable to a prosthetic leg;
applying pressure to the chamber in the socket with a vacuum source to form a vacuum within the chamber;
changing an amplitude of the fluid pressure applied by the vacuum source between predetermined amplitudes each in the range of between 30 and 760 mmHg to provide pressure therapy to the residuum; and
using the prosthetic leg to perform at least one of a weight-bearing phase of the stride, a non-weight bearing phase of the stride, a swing phase of the stride, standing, walking, and running.

61. The method of claim 60, wherein the changing step comprises controlling at least one of amplitude and frequency of the pressure.

62. The method of claim 60, wherein the changing step is carried out using at least one of a computer, microprocessor, and programmable controller.

63. The method of claim 60, wherein the predetermined pressure amplitudes comprise a first amplitude less than a pressure outside the socket and a second amplitude greater than the pressure outside the socket.

64. The method of claim 60, wherein the changing step is responsive to at least one of a weight-bearing phase of the stride, a swing phase of the stride, standing, walking, running, and non-weight-bearing.

65. The method of claim 60, wherein the changing step is responsive to a change in a volume of the residuum.

66. The method of claim 60, wherein the changing step comprises regulating the pressure within the chamber responsive to input from at least one of a blood flow sensor, blood gas sensor, temperature sensor, pressure sensor, heart rate sensor, residuum volume sensor, and residuum fluid volume sensor.

67. The method of claim 60, further comprising delivering medicine or drug to the residuum.

68. The method of claim 60, further comprising controlling a pressure gradient between zones of the chamber.

* * * * *